(12) United States Patent
Scherer et al.

(10) Patent No.: US 6,825,328 B1
(45) Date of Patent: Nov. 30, 2004

(54) LAFORA'S DISEASE GENE

(76) Inventors: Stephen W. Scherer, 60 Mayfield Avenue, Toronto, Ontario (CA), M6S 1K5; Berge A. Minassian, 18 Vanderhoff Avenue, Toronto, Ontario (CA), M4G 2H1; Antonio Delgado-Escueta, 28342 Rey De Copas La., Malibu, CA (US) 90265; Guy Rouleu, 4850 Cote St., Luc Road, Montreal, Quebec (CA), H3W 2H2

( * ) Notice: Subject to any disclaimer, the term of this patent is extended or adjusted under 35 U.S.C. 154(b) by 0 days.

(21) Appl. No.: 09/744,072
(22) PCT Filed: Jul. 20, 1999
(86) PCT No.: PCT/CA99/00646
§ 371 (c)(1),
(2), (4) Date: Jul. 2, 2001
(87) PCT Pub. No.: WO00/05405
PCT Pub. Date: Feb. 3, 2000

Related U.S. Application Data
(60) Provisional application No. 60/130,269, filed on Apr. 21, 1999, and provisional application No. 60/093,495, filed on Jul. 20, 1998.

(51) Int. Cl.[7] ............................................. C07H 21/04
(52) U.S. Cl. ...................... 536/23.1; 536/24.3; 435/195
(58) Field of Search .............................. 536/23.1, 24.3; 435/195

(56) References Cited
FOREIGN PATENT DOCUMENTS

EP          0705842 A2  *  4/1996

OTHER PUBLICATIONS

Denu et al. 1996 Cell, vol. 87, pp. 361–364;.*
Genbank Accession AJ130763, GI 3980308, Dec. 16, 1998.*
Minassian, B. et al, (Mutations in a gene encoding a novel protein tyrosine phosphatase cause progressive Myoclonus epilepsy), Natura Genetics, vol. 20, Oct. 1998, pp. 171–174.
Serratosa, J. et al., (A novel protein tyrosine phosphatase gene is mutated in progressive myoclonus epilepsy of the Lafora type (EPM2)), Human Molecular Genetics, vol. 8, No. 2, Feb. 1999, pp. 345–352.
Minassian, B. et al., (Progress Towards the Positional Cloning of a Gene for Lafora's Disease), Neuology, vol. 48, No. 3, Suppl. 2, Apr. 1997, p. A428.
Sainz, J. et al., (Lafora Progressive Myoclonus Epilepsy: Narrowing the Chromosome 6q24 Locus by Recombinations and Homozygosities), Amer. Journal of Human Genetics, vol. 61, No. 5, 1997, pp. 1205–09.
Minassian B. et al., (Genetic Locus Heterogeneity in Lafora's Progressive Myoclonus Epilepsy), American Neurological Assoc., 1999, pp. 262–265. Annals of Neurology.
Roes, J. et al. (Mouse anti–mouse IgD moncolonal antibodies generated in IID–deficient mice), Journal of Immunological Methods, 1995, pp. 231–237.

* cited by examiner

Primary Examiner—Jeffrey Fredman
Assistant Examiner—Juliet C. Switzer
(74) Attorney, Agent, or Firm—Foley & Lardner LLP

(57) ABSTRACT

Lafora's disease in humans is characterized by the mutation or deletion of an EPM2A gene, which encodes a protein, Laforin, having a tyrosine phosphatase domain. Many different sequence mutations, including microdeletions, in EPM2A co-segregate with, Lafora's disease. Accordingly, detection of mutations in EPM2 are useful in diagnosing Lafora's disease.

4 Claims, 17 Drawing Sheets

FIGURE 4 a

```
  1 GGTGGAGCTGGCGGCCGAGGAGGCGGCGCAGGACGGGGCGGAGCCGGGCCGCGTGGACAC
  1  V  E  L  A  A  E  E  A  A  Q  D  G  A  E  P  G  R  V  D  T
                                                             ↓
 61 GTTCTGGTACAAGTTCCTGAAGCGGGAGCCGGGAGGAGAGCTCTCCTGGGAAGGCAATGG
 21  F  W  Y  K  F  L  K  R  E  P  G  G  E  L  S  W  E  G  N  G

121 ACCTCATCATGACCGTTGCTGTACTTACAATGAAAACAACTTGGTGGATGGTGTGTATTG
 41  F  H  H  D  R  C  C  T  Y  N  E  N  N  L  V  D  G  V  V  C
                   C (LD5)          T (polymorphism)
181 TCTCCCAATAGGACACTGGATTGAGGCCACTGGACACACCAATGAAATGAAGCACACAAC
 61  L  P  I  G  H  W  I  E  A  T  G  H  T  N  E  M  K  H  T  T
                       (I-22) *                    ↓
241 AGACTTCTATTTTAATATTGCAGGCCACCAAGCCATCCATTATTCAAGAATTCTACCAAA
 81  D  F  Y  F  N  I  A  G  H  Q  A  M  H  Y  S  R  I  L  P  N 301 TATCTGGCTGGGTAGCTGCCCTCGACAGGTGGAACATGTTACCATCAAACTGAAGCATGA
101  I  W  L  G  S  C  P  R  Q  V  E  H  V  T  I  K  L  K  H  E 361 ATTGGGGATTACAGCTGTCATGAATTTCCAGACTGAATGGGATATTGTTCAGAATTCCTC
121  L  G  I  T  A  V  M  N  F  Q  T  E  W  D  I  V  Q  N  S  S 421 ATGCTGTAACCGCTACCCAGAGCCCATGACTCCAGACACTATGATTAAACTATCTAGGGA
141  C  C  N  R  Y  P  E  P  M  T  P  D  T  M  I  K  L  S  R  E
                                                          ↓
481 AGAAGGCTTGGCCTACATCTGGATGCCAACACCAGATATGAGCACCGCAGGCCGAGTACA
161  E  G  L  A  Y  I  W  M  P  T  P  D  M  S  T  A  G  R  V  Q
                                                    (6 families) *
541 GATGCTGCCCCAGGCGGTGTGCCTGCTGCATGCGCTGCTGGAGAAGGGACACATCGTGTA
181  M  L  P  Q  A  V  C  L  L  H  A  L  L  E  K  G  H  I  V  Y
              ▼A insertion (LD100)
601 CGTGCACTGCAACGCTGGGGTGGGCCGCTCCACCGCGGCTGTCTGCGGCTGGCTCCAGTA
201  |V  H  C  N  A  G  V  G  R  S  T| A  A  V  C  G  W  L  Q  Y
                                                  S (L6)
661 TGTGATGGGCTGGAATCTGAGGAAGGTGCAGTATTTCCTCATGGCCAAGAGGCCGGCTGT
221  V  M  G  W  N  L  R  K  V  Q  Y  F  L  M  A  K  R  P  A  V
                                              L (LD33)
721 CTACATTGACGAAGAGGCCTTGGCCCGGGCACAAGAAGATTTTTTCCAGAAATTTGGGAA
241  Y  I  D  E  E  A  L  A  R  A  Q  E  D  F  F  Q  K  F  G  K 781 GGTTCGTTCTTCTGTGTGTAGCCTGTAGctggtcagcctgcttctgcccctcctgattt
261  V  R  S  S  V  C  S  L  *

841 ccctaaggagcctgggatgatgttggtcaaatgacctagaaacaaggattctacctgaac
 901 tgaaggactgtgtgacctccccaagccaaccactttcacctgggatgacttcgattat
 961 gctttggtttggggctgtattttgaaatactctacaagaaagctgtggctcaacacatg
1021 agaagaagcacgaagcagttaggctgtacatcagacagaagggtaatgcgtgcagttcct
1081 gctgcctgcaggcagacgaggcctttgctttacagcactgtatgtgttgcacgatggatc
1141 cgtgacagcactttcctgttgcactgaaactcttggccatgtagaggaaaagatatggag
1201 ttatgtggatttcatcactagtatgtgtgccgtgagctggtcagttgccaaaggaggaaa
1261 taaggttagaagcctgaaccgttacaaaagaagagctcactatggtcaaaaagtgatggc
1321 tttcaggacttgtttttttatcctgcctcacagttgttaaagtctgttccaaggcatcacc
1381 ttccttctctacccaacaaccctgtgtaacaactaaagtagaattatctctcattcgttcg
1441 gtggttttcctcaaaattaccaaacaaagcaaaaaataacccttgttttttatagttgag
1501 atgtcaaggaagttaaattgaggcttaatgagcataggtagcttgtccaaggtctcatga
1561 ccagtcaagggcaagctggagttaataatctatattttattcgactcagcactgttttcat
1621 cacaacttgttttcccagcatcatgtagtgcatttagttttgtcttctcagggtatagt
1681 caatatgcctgcaggagtttctatagcgagacatagaatagtattctgatcagttgccaa
1741 agaatctaggaaattagttgtattttgtgcaagctaatttaaaaacatgatgggctgttt
1801 taagaccagagtggaaattcatgagaggaactatactaccaaaagagcccaaatgaccaa
1861 atccatggataattgcttcacagcccttggccatcctggctcagctctcaattcagtataa
1921 tatgcagttcctgtgcctccagactatgcagctcatcaccctaggttctacaggaaatac
1981 agagatgaacaacttttgccttcaaaaaatgtgctgcctagaaaacagacctgcattcaa
2041 cccaactgtaatgcaggatttggaccatgaatgatatgctagaatagaagaaagagaagt
2101 gtttttttaattgagagcctctatgtgcaaggtgatatataatcatatccagtttaatct
2161 tcacaatatccaatgaagaaggtctcattatctccatgataaagatgggaaactaaggt
2221 cagaagggttaactcaactgtctattgtcacatgatgaataaatagatgaagtgagatac
2281 aaagctgggtttgattcaaagcccttactttcctaattaaactatgatgcgtatttattt
2341 ttctgcaccttccttttcttccacaaacacatattgatagatgcaagagactcttattat
2401 aaggcgtgggggacaagaaggatacaaggtaagtttcagtggagctcagaggacggggag
2461 atagaactgtggcacttaggggagatgacattgcttgggcagagcgagctagccagga
2521 cacattccactataattttacaaagttaaatttataagctagcattaagtaaagtgaag
2581 tccagctccttgctaaaaataactagaggtaataattggtattcaggtaactcatttac
2641 agtcataatgtgttgtgaaaatttaatcttaaaaattaaattttttaaactatgtgggtct
2701 gtgaatttctttaatgtctaagaaatccagcttcataattctcatgatacaaagatcttt
2761 tttcaggtggatttttacctttgttccttttgctctgatagacaaaatcagtttaggact
2821 attaaagaatgttttgg aataaaa tgtcttttcctcaatgaatgggatgtctaatgtat
2881 ttcaaaatcacccaaaa ttttgg ca aataaaa gcatttaaaaagaaaaaaaaaaaaaa
``` b

amino acid # 1  247

• LARAQEDFFQKFGKVRSSVCSL
• ASQDTFPL c

| | |
|---|---|
| LD1 | VHCNAGVGRST |
| MTM1 | VHCSDGWDRTA |
| PTEN | IHCKAGKGRTG |
| PTP1B | VHCSAGIGRSG |
| dPTP61F | VHCSAGIGRSG |
| virus | VHCQAGISRSA |

FIGURE 7 (P1)

LDA

LDA.seq Length: 2940 July 16, 1998 10:34 Type: N Check: 4100 ..

```
   1 GGTGGAGCTG GCGGCCGAGG AGGCGGCGCA GGACGGGGCG GAGCCGGGCC
  51 GCGTGGACAC GTTCTGGTAC AAGTTCCTGA AGCGGGAGCC GGGAGGAGAG
 101 CTCTCCTGGG AAGGCAATGG ACCTCATCAT GACCGTTGCT GTACTTACAA
 151 TGAAAACAAC TTGGTGGATG GTGTGTATTG TCTCCCAATA GGACACTGGA
 201 TTGAGGCCAC TGGACACACC AATGAAATGA AGCACACAAC AGACTTCTAT
 251 TTTAATATTG CAGGCCACCA AGCCATGCAT TATTCAAGAA TTCTACCAAA
 301 TATCTGGCTG GGTAGCTGCC CTCGACAGGT GGAACATGTT ACCATCAAAC
 351 TGAAGCATGA ATTGGGGATT ACAGCTGTCA TGAATTTCCA GACTGAATGG
 401 GATATTGTTC AGAATTCCTC ATGCTGTAAC CGCTACCCAG AGCCCATGAC
 451 TCCAGACACT ATGATTAAAC TATCTAGGGA AGAAGGCTTG GCCTACATCT
 501 GGATGCCAAC ACCAGATATG AGCACCGCAG GCCGAGTACA GATGCTGCCC
 551 CAGGCGGTGT GCCTGCTGCA TGCGCTGCTG GAGAAGGGAC ACATCGTGTA
 601 CGTGCACTGC AACGCTGGGG TGGGCCGCTC CACCGCGGCT GTCTGCGGCT
 651 GGCTCCAGTA TGTGATGGGC TGGAATCTGA GGAAGGTGCA GTATTTCCTC
 701 ATGGCCAAGA GGCCGGCTGT CTACATTGAC GAAGAGGCCT TGGCCCGGGC
 751 ACAAGAAGAT TTTTTCCAGA AATTTGGGAA GGTTCGTTCT TCTGTGTGTA
 801 GCCTGTAGCT GGTCAGCCTG CTTCTGCCCC CTCCTGATTT CCCTAAGGAG
 851 CCTGGGATGA TGTTGGTCAA ATGACCTAGA AACAAGGATT CTACCTGAAC
 901 TGAAAGGACT GTGTGACCTC CCCAAGCCAA CCACTTTCAC CTGGGATGAC
 951 TTTCGATTAT GCTTTGGTTT GGGGCTGTAT TTTTGAAATA CTCTACAAGA
1001 AAGCTGTGGC TCAACACATG AGAAGAAGCA CGAAGCAGTT AGGCTGTACA
1051 TCAGACAGAA GGGTAATGCG TGCAGTTCCT GCTGCCTGCA GGCAGACGAG
1101 GCCTTTGCTT TACAGCACTG TATGTGTTGC ACGATGGATC CGTGACAGCA
1151 CTTTCCTGTT GCACTGAAAC TCTTGGCCAT GTAGAGGAAA AGATATGGAG
1201 TTATGTGGAT TTCATCACTA GTATGTGTGC CGTGAGCTGG TCAGTTGCCA
1251 AAGGAGGAAA TAAGGTTAGA AGCCTGAACC GTTACAAAAG AAGAGCTCAC
```

FIGURE 7 (P2)

```
1301 TATGGTCAAA AAGTGATGGC TTTCAGGACT TGTTTTTTAT CCTGCCTCAC
1351 AGTTGTTAAA GTCTGTTCCA AGGCATCACC TTCCTTCTCT ACCCAACAAC
1401 CCTGTGTAAC AACTAAAGTA GAATTATCTC TCATTTGTTG GTGGTTTTTC
1451 CTCAAAATTA CCAAACAAAG CAAAAAATAC CCTTGTTTTT TATAGTTGAG
1501 ATGTCAAGGA AGTTAAATTG AGGCTTAATG AGCATAGGTA GCTTGTCCAA
1551 GGTCTCATGA CCAGTCAAGG GCAAGCTGGA GTTAATAATC TATATTTATT
1601 TGACTCAGCA CTGTTTTCAT CACAACTTGT TTTCCCAGCA TCATGTAGTG
1651 CATTTAGTTT TGTCTTTCTC AGGGTATAGT CAATATGCCT GCAGGAGTTT
1701 CTATAGCGAG ACATAGAATA GTATTCTGAT CAGTTGCCAA AGAATCTAGG
1751 AAATTAGTTG TATTTTGTGC AAGCTAATTT AAAAACATGA TGGGCTGTTT
1801 TAAGACCAGA GTGGAAATTC ATGAGAGGAA CTATACTACC AAAAGAGCCC
1851 AAATGACCAA ATCCATGGAT AATTGCTTCA CAGCCTTGGC CATCCTGGCT
1901 CAGCTCTCAA TTTAGTATAA TATGCAGTTC CTGTGCCTCC AGACTATGCA
1951 GCTCATCACC CTAGGTTCTA CAGGAAATAC AGAGATGAAC AACTTTGCCT
2001 TCAAAAAATG TGCTGCCTAG AAAACAGACC TGCATTTCAA CCCAACTGTA
2051 ATGCAGGATT TGGACCATGA ATGATATGCT AGAATAGAAG AAAGAGAAGT
2101 GTTTTTTTAA TTGAGAGCCT CTATGTGCAA GGTGATATAT AATCATATCC
2151 AGTTTAATCT TCACAATATC CAATGAAGAA GGTCTCATTA TCTCCATGAT
2201 AAAGATGGGG AAACTAAGGT CAGAAGGGTT AACTCAACTG TCTATTGTCA
2251 CATGATGAAT AAATAGATGA AGTGAGATAC AAAGCTGGGT TTGATTCAAA
2301 GCCCTTACTT TCCTAATTAA ACTATGATGC GTATTTATTT TTCTGCACCT
2351 TCCTTTCTTC CACAAACACA TATTGATAGA TGCAAGAGAC TCTTATTTAT
2401 AAGGCGTGGG GGACAAGAAG GATACAAGGT AAGTTTCAGT GGAGCTCAGA
2451 GGACGGGGAG ATAGAACTGT GGCACTTAGG GGAGATGACA TTTGCTTTGG
2501 GCAGAGGCAG CTAGCCAGGA CACATTTCCA CTATAATTTT ACAAAGTTAA
2551 ATTTATAAGC TAGCATTAAG TAAAGTGAAG TCCAGCTCCC TTGCTAAAAA
2601 TAACTAGAGG TAATAATTGG TATTCAGGTA ACTCATTTAC AGTCATAATG
2651 TGTTGTGAAA ATTTAATCTT AAAAATTAAA TTTTTAAACT ATGTGGGTCT
```

FIGURE 7 (P3)

```
2701 GTGAATTTCT TTAATGTCTA AGAAATCCAG CTTCATAATT TCCATGATAC
2751 AAAGATCTTT TTTCAGGTGG ATTTTTACCT TTGTTCCTTT TGCTCTGATA
2801 GACAAAATCA GTTTAGGACT ATTAAAGAAT GTTTTGGAAT AAACTGTCTT
2851 TTTCCTCAAT GAATGGGATG TCTAATGTAT TTCAAAATCA CCCAAAACTT
2901 TTGGCAAATA AAGCATTTA AAAAGAAAAA AAAAAAAAAA
```

FIGURE 8

LDA.pep Length: 268 July 16, 1998 10:33 Type: P Check: 9839 ..

1 VELAAEEAAQ DGAEPGRVDT FWYKFLKREP GGELSWEGNG PHHDRCCTYN

51 ENNLVDGVYC LPIGHWIEAT GHTNEMKHTT DFYFNIAGHQ AMHYSRILPN

101 IWLGSCPRQV EHVTIKLKHE LGITAVMNFQ TEWDIVQNSS CCNRYPEPMT

151 PDTMIKLSRE EGLAYIWMPT PDMSTAGRVQ MLPQAVCLLH ALLEKGHIVY

201 VHCNAGVGRS TAAVCGWLQY VMGWNLRKVQ YFLMAKRPAV YIDEEALARA

251 QEDFFQKFGK VRSSVCSL

FIGURE 9

LDB.seq Length: 915 July 16, 1998 10:34 Type: N Check: 2239 ..

```
  1 CCAAGAATCG GCACGAGGAT TATTCAAGAA TTCTACCAAA TATCTGGCTG
 51 GGTAGCTGCC CTCGACAGGT GGAACATGTT ACCATCAAAC TGAAGCATGA
101 ATTGGGGATT ACAGCTGTCA TGAATTTCCA GACTGAATGG GATATTGTTC
151 AGAATTCCTC ATGCTGTAAC CGCTACCCAG AGCCCATGAC TCCAGACACT
201 ATGATTAAAC TATCTAGGGA AGAAGGCTTG GCCTACATCT GGATGCCAAC
251 ACCAGATATG AGCACCGCAG GCCGAGTACA GATGCTGCCC CAGGCGGTGT
301 GCCTGCTGCA TGCGCTGCTG GAGAAGGGAC ACATCGTGTA CGTGCACTGC
351 AACGCTGGGG TGGGCCGCTC CACCGCGGCT GTCTGCGGCT GGCTCCAGTA
401 TGTGATGGGC TGGAATCTGA GGAAGGTGCA GTATTTCCTC ATGGCCAAGA
451 GGCCGGCTGT CTACATTGAC GAAGAGGCAG CTAGCCAGGA CACATTTCCA
501 CTATAATTTT ACAAAGTTAA ATTTATAAGC TAGCATTAAG TAAAGTGAAG
551 TCCAGCTCCC TTGCTAAAAA TAACTAGAGG TAATAATTGG TATTCAGGTA
601 ACTCATTTAC AGTCATAATG TGTTGTGAAA ATTTAATCTT AAAAATTAAA
651 TTTTTAAACT ATGTGGGTCT GTGAATTTCT TTAATGTCTA AGAAATCCAG
701 CTTCATAATT TCCATGATAC AAAGATCTTT TTTCAGGTGG ATTTTTACCT
751 TTGTTCCTTT TGCTCTGATA GACAAAATCA GTTTAGGACT ATTAAAGAAT
801 GTTTTGGAAT AAACTGTCTT TTTCCTCAAT GAATGGGATG TCTAATGTAT
851 TTCAAAATCA CCCAAAACTT TTGGCAAATA AAGCATTTA AAAAGAAAAA
901 AAAAAAAAAA AAAAA
```

FIGURE 10

LDB.pep Length: 167 July 16, 1998 10:34 Type: P Check: 3130 ..

1   KNRHEDYSRI LPNIWLGSCP RQVEHVTIKL KHELGITAVM NFQTEWDIVQ

51  NSSCCNRYPE PMTPDTMIKL SREEGLAYIW MPTPDMSTAG RVQMLPQAVC

101 LLHALLEKGH IVYVHCNAGV GRSTAAVCGW LQYVMGWNLR KVQYFLMAKR

151 PAVYIDEEAA SQDTFPL

FIGURE 12
A.
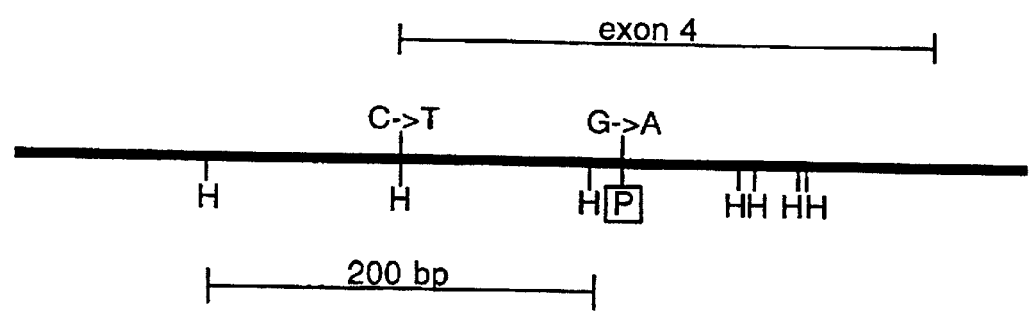
B.
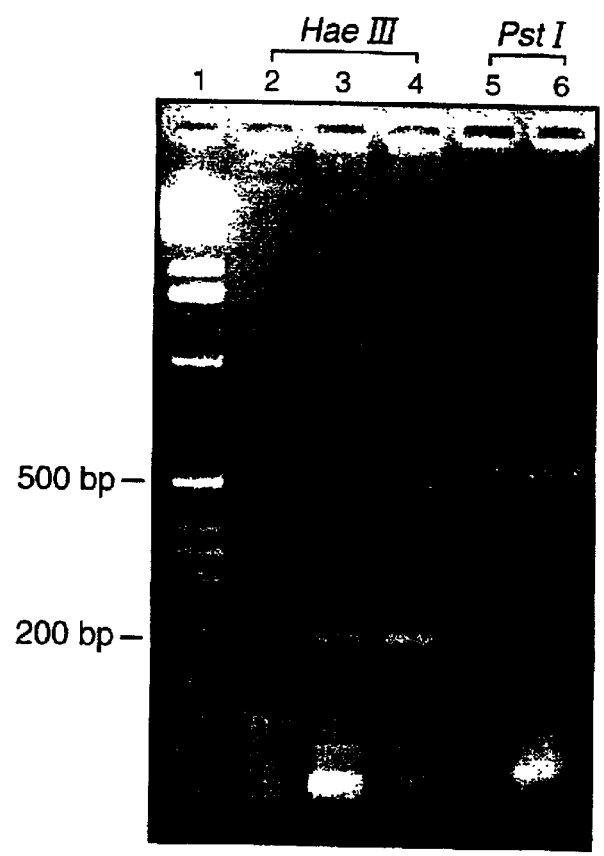

FIGURE 13 (P1)

```
   1  ATGCGCTTCC GCTTTGGGGT GGTGGTGCCA CCCGCCGTGG CCGGCGCCCG
  51  GCCGGAGCTG CTGGTGGTGG GGTCGCGGCC CGAGCTGGGG CGTTGGGAGC
 101  CGCGCGGTGC CGTCCGCCTG AGGCCGGCCG GCACCGCGGC GGGCGACGGG
 151  GCCCTGGCGC TGCAGGAGCC GGGCCTGTGG CTCGGGGAGG TGGAGCTGGC
 201  GGCCGAGGAG GCGGCGCAGG ACGGGCGGA GCCGGGCCGC GTGGACACGT
 251  TCTGGTACAA GTTCCTGAAG CGGGAGCCGG GAGGAGAGCT CTCCTGGGAA
 301  GGCAATGGAC CTCATCATGA CCGTTGCTGT ACTTACAATG AAAACAACTT
 351  GGTGGATGGT GTGTATTGTC TCCCAATAGG ACACTGGATT GAGGCCACTG
 401  GGCACACCAA TGAAATGAAG CACACAACAG ACTTCTATTT TAATATTGCA
 451  GGCCACCAAG CCATGCATTA TTCAAGAATT CTACCAAATA TCTGGCTGGG
 501  TAGCTGCCCT CGTCAGGTGG AACATGTTAC CATCAAACTG AAGCATGAAT
 551  TGGGGATTAC AGCTGTAATG AATTTCCAGA CTGAATGGGA TATTGTACAG
 601  AATTCCTCAG GCTGTAACCG CTACCCAGAG CCCATGACTC CAGACACTAT
 651  GATTAAACTA TATAGGGAAG AAGGCTTGGC CTACATCTGG ATGCCAACAC
 701  CAGATATGAG CACCGAAGGC CGAGTACAGA TGCTGCCCCA GGCGGTGTGC
 751  CTGCTGCATG CGCTGCTGGA GAAGGGACAC ATCGTGTACG TGCACTGCAA
 801  CGCTGGGGTG GGCCGCTCCA CCGCGGCTGT CTGCGGCTGG CTCCAGTATG
 851  TGATGGGCTG GAATCTGAGG AAGGTGCAGT ATTTCCTCAT GGCCAAGAGG
 901  CCGGCTGTCT ACATTGACGA AGAGGCCTTG GCCCGGGCAC AAGAAGATTT
 951  TTTCCAGAAA TTTGGGAAGG TTCGTTCTTC TGTGTGTAGC CTGTAGCTGG
1001  TCAGCCTGCT TCTGCCCCCT CCTGATTTCC CTAAGGAGCC TGGGATGATG
1051  TTGGTCAAAT GACCTAGAAA CAAGGATTCT ACCTGAACTG AAAGGACTGT
1101  GTGACCTCCC CAAGCCAACC ACTTTCACCT GGGATGACTT TCGATTATGC
1151  TTTGGTTTGG GGCTGTATTT TTGAAATACT CTACAAGAAA GCTGTGGCTC
1201  AACACATGAG AAGAAGCACG AAGCAGTTAG GCTGTACATC AGACAGAAGG
1251  GTAATGCGTG CAGTTCCTGC TGCCTGCAGG CAGACGAGGC CTTTGCTTTA
1301  CAGCACTGTA TGTGTTGCAC GATGGATCCG TGACAGCACT TTCCTGTTGC
1351  ACTGAAACTC TTGGCCATGT AGAGGAAAAG ATATGGAGTT ATGTGGATTT
1401  CATCACTAGT ATGTGTGCCG TGAGCTGGTC AGTTGCCAAA GGAGGAAATA
1451  AGGTTAGAAG CCTGAACCGT TACAAAAGAA GAGCTCACTA TGGTCAAAAA
1501  GTGATGGCTT TCAGGACTTG TTTTTTATCC TGCCTCACAG TTGTTAAAGT
1551  CTGTTCCAAG GCATCACCTT CCTTCTCTAC CCAACAACCC TGTGTAACAA
1601  CTAAAGTAGA ATTATCTCTC ATTTGTTGGT GGTTTTTCCT CAAAATTACC
1651  AAACAAAGCA AAAAATACCC TTGTTTTTTA TAGTTGAGAT GTCAAGGAAG
1701  TTAAATTGAG GCTTAATGAG CATAGGTAGC TTGTCCAAGG TCTCATGACC
1751  AGTCAAGGGC AAGCTGGAGT TAATAATCTA TATTTATTTG ACTCAGCACT
1801  GTTTTCATCA CAACTTGTTT TCCCAGCATC ATGTAGTGCA TTTAGTTTTG
```

FIGURE 13 (P2)

```
1851 TCTTTCTCAG GGTATAGTCA ATATGCCTGC AGGAGTTTCT ATAGCGAGAC
1901 ATAGAATAGT ATTCTGATCA GTTGCCAAAG AATCTAGGAA ATTAGTTGTA
1951 TTTTGTGCAA GCTAATTTAA AAACATGATG GGCTGTTTTA AGACCAGAGT
2001 GGAAATTCAT GAGAGGAACT ATACTACCAA AAGAGCCCAA ATGACCAAAT
2051 CCATGGATAA TTGCTTCACA GCCTTGGCCA TCCTGGCTCA GCTCTCAATT
2101 TAGTATAATA TGCAGTTCCT GTGCCTCCAG ACTATGCAGC TCATCACCCT
2151 AGGTTCTACA GGAAATACAG AGATGAACAA CTTTGCCTTC AAAAAATGTG
2201 CTGCCTAGAA AACAGACCTG CATTTCAACC CAACTGTAAT GCAGGATTTG
2251 GACCATGAAT GATATGCTAG AATAGAAGAA AGAGAAGTGT TTTTTTAATT
2301 GAGAGCCTCT ATGTGCAAGG TGATATATAA TCATATCCAG TTTAATCTTC
2351 ACAATATCCA ATGAAGAAGG TCTCATTATC TCCATGATAA AGATGGGGAA
2401 ACTAAGGTCA GAAGGGTTAA CTCAACTGTC TATTGTCACA TGATGAATAA
2451 ATAGATGAAG TGAGATACAA AGCTGGGTTT GATTCAAAGC CCTTACTTTC
2501 CTAATTAAAC TATGATGCGT ATTTATTTTT CTGCACCTTC CTTTCTTCCA
2551 CAAACACATA TTGATAGATG CAAGAGACTC TTATTTATAA GGCGTGGGGG
2601 ACAAGAAGGA TACAAGGTAA GTTTCAGTGG AGCTCAGAGG ACGGGGAGAT
2651 AGAACTGTGG CACTTAGGGG AGATGACATT TGCTTTGGGC AGAGGCAGCT
2701 AGCCAGGACA CATTTCCACT ATAATTTTAC AAAGTTAAAT TTATAAGCTA
2751 GCATTAAGTA AAGTGAAGTC CAGCTCCCTT GCTAAAAATA ACTAGAGGTA
2801 ATAATTGGTA TTCAGGTAAC TCATTTACAG TCATAATGTG TTGTGAAAAT
2851 TTAATCTTAA AAATTAAATT TTTAAACTAT GTGGGTCTGT GAATTTCTTT
2901 AATGTCTAAG AAATCCAGCT TCATAATTTC CATGATACAA AGATCTTTTT
2951 TCAGGTGGAT TTTTACCTTT GTTCCTTTTG CTCTGATAGA CAAAATCAGT
3001 TTAGGACTAT TAAAGAATGT TTTGGAATAA ACTGTCTTTT TCCTCAATGA
3051 ATGGGATGTC TAATGTATTT CAAAATCACC CAAAACTTTT GGCAAATAAA
3101 AGCATTTAAA AAGAAAAAAA AAAAAAA
```

FIGURE 14

MRFRFGVVVPPAVAGARPELLVVGSRPELGRWEPRGAVRLRPAGTAAGDG
ALALQEPGLWLGEVELAAEEAAQDGAEPGRVDTFWYKFLKREPGGELSWE
GNGPHHDRCCTYNENNLVDGVYCLPIGHWIEATGHTNEMKHTTDFYFNIA
GHQAMHYSRILPNIWLGSCPRQVEHVTIKLKHELGITAVMNFQTEWDIVQ
NSSGCNRYPEPMTPDTMIKLYREEGLAYIWMPTPDMSTEGRVQMLPQAVC
LLHALLEKGHIVYVHCNAGVGRSTAAVCGWLQYVMGWNLRKVQYFLMAKR
PAVYIDEEALARAQEDFFQKFGKVRSSVCSL

LAFORA'S DISEASE GENE

This application is a national phase entry application of PCT/CA99/00646 filed Jul. 20, 1999, which claims priority from U.S. provisional application No. 60/130,269 filed Apr. 21, 1999 (now abandoned) and U.S. provisional application No. 60/093,495 filed Jul. 20, 1998 (now abandoned), all of which are incorporated herein by reference in their entirety.

FIELD OF THE INVENTION

The invention relates to a novel gene, EPM2A, that is involved in Lafora's disease; the protein, Laforin, encoded by the gene; and methods of diagnosing and treating Lafora's disease.

BACKGROUND OF THE INVENTION

The epilepsies constitute one of the most common neurological disorders affecting 40 million people worldwide (1). Within the spectrum of epileptic syndromes is a group of heterogeneous inherited disorders named the Progressive Myoclonus Epilepsies (PME) in which progressive neurological decline and worsening primarily myoclonic seizures follow an initial period of normal development (2,3,4). Lafora's disease (LD) is an autosomal recessive and genetically heterogeneous form of Progressive Myoclonus Epilepsy characterized by polyglucosan inclusions seizures and cumulative neurological deterioration. The onset occurs during late childhood and usually results in death within a decade of first symptoms. With few exceptions, patients with LD follow a homogeneous clinical course (4) despite the existence of genetic locus heterogeneity (5). Biopsy (or autopsy) of various tissues including brain, liver, muscle, and skin reveals characteristic periodic acid-Schiff positive polyglucosan inclusions (Lafora bodies) (6–9). Substantial biochemical and histological studies of these bodies suggest LD is a generalized storage disease (8,10,11), but the presumed enzymatic defect remains unknown.

Linkage analysis and homozygosity mapping initially localized a Lafora's disease locus (EPM2A) to a region at chromosome 6q23–q25 bounded by the genetic markers D6S1003 and D6S311 (12,13). However, there is a need in the art to more clearly define the region(s) mutated in Lafora's disease to allow for the development of accurate diagnostic assays for Lafora's disease. More specifically, there is a need to sequence; the gene associated with Lafora's Disease and to identify mutations and/or deletions in the gene that are causative of Lafora's Disease.

SUMMARY OF THE INVENTION

The present inventors have identified a novel gene, EPM2A, that is deleted or mutated in people with Lafora's disease. Using a positional cloning approach the inventors have identified at chromosome 6q24 the EPM2A gene that encodes a protein with consensus amino acid sequence indicative of a tyrosine phosphatase. Accordingly, the present invention provides an isolated nucleic acid molecule containing a sequence encoding an active catalytic site of a protein tyrosine phosphatase which is associated with Lafora's disease.

In one embodiment of the invention, an isolated nucleic acid molecule is provided having a sequence as shown in SEQ.ID.NO.:1 or FIG. 13.

Preferably, the purified and isolated nucleic acid molecule comprises:

(a) a nucleic acid sequence as shown in SEQ.ID.NO.:1 and FIG. 13, wherein T can also be U;

(b) nucleic acid sequences complementary to (a);

(c) nucleic acid sequences which are homologous to (a) or (b);

(d) a fragment of (a) to (c) that is at least 15 bases, preferably 20 to 30 bases, and which will hybridize to (a) to (d) under stringent hybridization conditions; or (e) a nucleic acid molecule differing from any of the nucleic acids of (a) to (c) in codon sequences due to the degeneracy of the genetic code.

Fourteen different mutations in EPM2A in 24 families have been found that co-segregate with Lafora's disease. These alterations would be predicted to abolish or cause deleterious effects on the protein product, Laforin, resulting in the primary defect in a large portion of patients with the disease. Accordingly, the present invention provides a method of detecting Lafora's disease comprising detecting a mutation or deletion in the EPM2A gene in a sample from a mammal. A mutation can be detected by sequencing the EPM2A gene, in particular in the region in the gene between markers D6S1003 and D6S1042, in a patient and comparing the sequence to the wild type EPM2A sequence shown in FIG. 13 to determine if a mutation or deletion is present. A mutation or deletion can also be detected by assaying for the protein product encoded by EPM2A, Laforin.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 4A is the nucleotide sequence (SEQ ID NO: 3) and predicted amino acid sequence (SEQ ID NO: 4) of EPM2A (incomplete).

FIG. 4B is an amino acid sequence of the carboxy terminus of transcript A (SEQ ID NO: 25) compared to transcript B (SEQ ID NO: 26).

FIG. 4C shows the PTP action sites (SEQ ID NOS: 27–32, respectively) of EPMA2A, MTMI (Swiss post. C13496), PTEN (Swiss post, 000633, PTP 1B (Swiss post APT P61F (GenBank L14849) and viral PTP (Swiss post Af 003534).

FIG. 7 is a nucleotide sequence of transcript A cDNA of the EPM2A gene (SEQ.ID.NO.:3).

FIG. 8 is the predicted amino acid sequence of transcript A (SEQ.ID.NO.:4).

FIG. 9 is a nucleotide sequence of transcript B cDNA of the EPM2A gene (SEQ.ID.NO.:5).

FIG. 10 is the predicted amino acid sequence of transcript B (SEQ.ID.NO.:6).

FIG. 12A is a restriction map of PCR products with primers H1F/PTPR.

FIG. 12B is the HaeIII and PstI digestion of the H1F/PTPR PCR product.

FIG. 13 is the complete nucleic acid sequence of EPM2A. This is also shown in SEQ.ID.NO.:1.

FIG. 14 is the complete amino acid sequence of EPM2A. This is also shown in SEQ.ID.NO.:2.

DETAILED DESCRIPTION OF THE INVENTION

Figure 1:
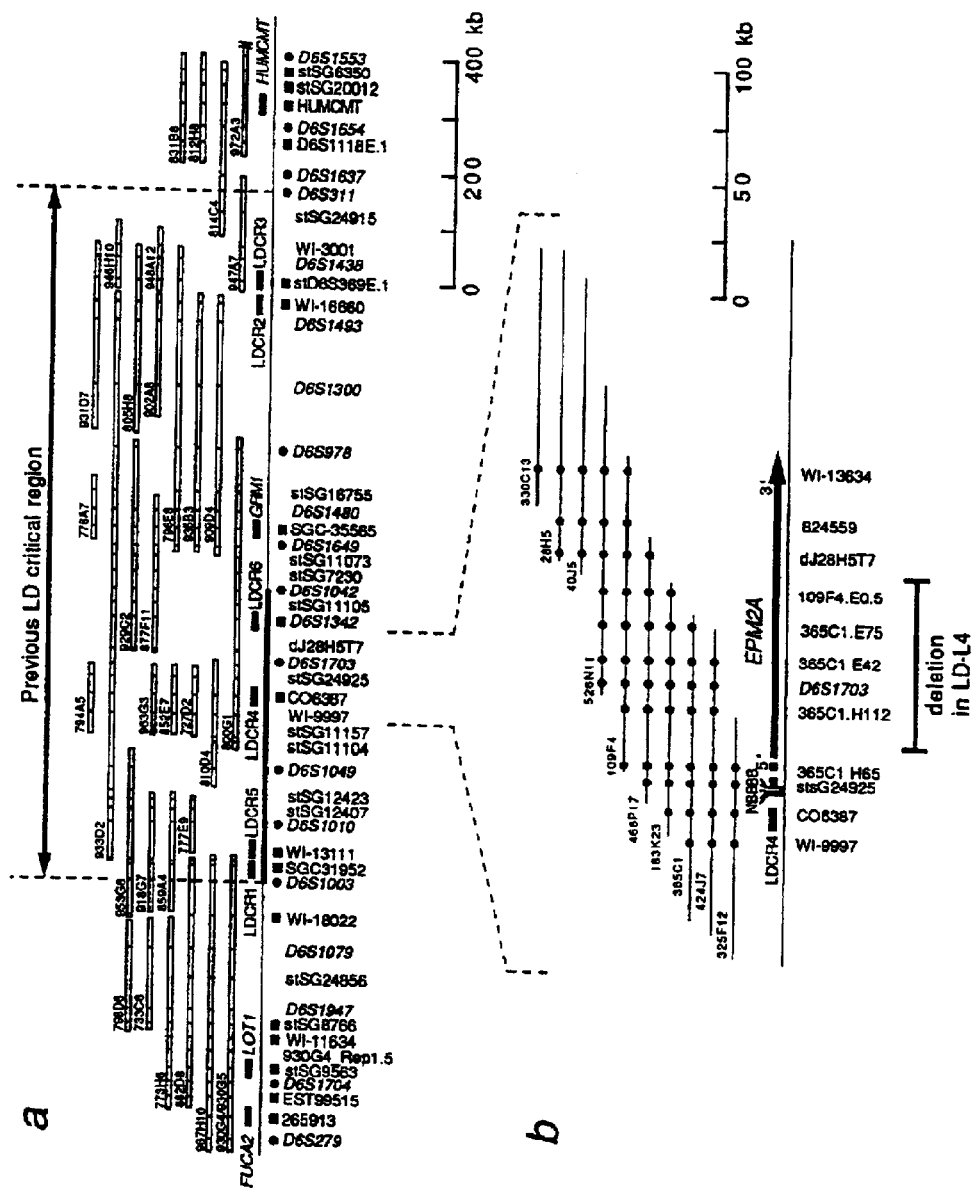
FIG. 1 is a physical map of the Lafora's disease critical region.

The present inventors constructed a high resolution physical map across the EPM2A gene to provide additional genetic and physical mapping reagents for refined localization of the disease gene. It was determined that the previously established critical region encompassed approximately 1.2 Mb of DNA. The map allowed the positioning of the location of 7 genetic markers, the metabotropic glutamate receptor 1 (GRM1) gene, and 6 expressed sequence tags (EST) clusters (tentatively named LDCR1–LDCR6), within the interval (FIG. 1). The genetic markers were then used to test for regions of homozygosity in each of the 30 families with Lafora's disease that appeared genotypically to arise due to mutations in a gene at 6q23–q25. In a single family; (LD39), an extended chain of homozygous markers within the previously established critical region allowed the inventors to, tentatively, redefine the telomeric boundary at D6S1042 (FIG. 2A). Simultaneously, a homozygous deletion of marker D6S1703 in the affected of a consanguineous family (LD-L4) (FIG. 2B) was detected. This observation confirmed the newly defined critical region to that 600 kb of DNA between D6S1003 and D6S1042, but more importantly, pinpointed the site of the disease gene within this region.

I. Nucleic Acid Molecules of the Invention

As hereinbefore mentioned, the present invention relates to isolated nucleic acid molecules that are involved in Lafora's disease. The term "isolated" refers to a nucleic acid substantially free of cellular material or culture medium when produced by recombinant DNA techniques, or chemical precursors, or other chemicals when chemically synthesized. The term "nucleic acid" is intended to include DNA and RNA and can be either double stranded or single stranded.

Broadly stated, the present invention provides an isolated nucleic acid molecule containing a sequence encoding an active catalytic site of a protein tyrosine phosphatase which is associated with Lafora's disease. The isolated nucleic acid molecule is preferably the EPM2A gene associated with Lafora's disease. In an embodiment of the invention, the isolated nucleic acid molecule has a sequence as shown in SEQ.ID.NO.:1 and FIG. 13.

Preferably, the purified and isolated nucleic acid molecule comprises (a) a nucleic acid sequence as shown in SEQ.ID.NO.:1 and FIG. 13, wherein T can also be U;

(b) nucleic add sequences complementary to (a);

(c) nucleic add sequences which are homologous to (a) or (b);

(d) a fragment of (a) to (c) that is at least 15 bases, preferably 20 to 30 bases, and which will hybridize to (a) to (d) under stringent hybridization conditions; or (e) a nucleic acid molecule differing from any of the nucleic adds of (a) to (c) in codon sequences due to the degeneracy of the genetic code.

The inventors have also isolated alternate forms of EPM2A which are generally referred to as transcript A and transcript B, herein. The nucleic acid 'sequence of transcript A is shown in SEQ.ID.NO.:3 and FIG. 7. The nucleic acid sequence of transcript B is shown in SEQ.ID.NO.:5 and FIG. 9. The amino acid sequence encoded by transcript A is shown in SEQ.ID.NO.:4 and FIG. 8. The amino acid sequence encoded by transcript B is shown in SEQ.ID.NO.:6 and FIG. 10.

The nucleic acid sequences shown in SEQ.ID.NOS.: 1, 3 and 5 (or FIGS. 13, 7 and 9, respectively) can be collectively referred to herein as "the nucleic acid molecules of the invention". The amino acid sequences shown in SEQ.ID.NOS.: 2,4 and 6 (or FIGS. 4A, 8 and 10, respectively) may be collectively referred to herein as the "proteins of the invention".

It will be appreciated that the invention includes nucleic acid molecules encoding truncations of the proteins of the invention, and analogs and homologs of the proteins of the invention and truncations thereof, as described below. It will further be appreciated that variant forms of the nucleic acid molecules of the invention which arise by alternative splicing of an mRNA corresponding to a cDNA of the invention are encompassed by the invention.

Further, it will be appreciated that the invention includes nucleic acid molecules comprising nucleic acid sequences having substantial sequence homology with the nucleic acid sequences of the invention and fragments thereof. The term "sequences having substantial sequence homology" means those nucleic acid sequences which have slight or inconsequential sequence variations from these sequences, i.e. the sequences function in substantially the same manner to produce functionally equivalent proteins. The variations may be attributable to local mutations or structural modifications.

Generally, nucleic acid sequences having substantial homology include nucleic acid sequences having at least 70%, preferably 80–90% identity with the nucleic acid sequences of the invention.

Another aspect of the invention provides a nucleic acid molecule, and fragments thereof having at least 15 bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, the following may be employed: 60×sodium chloride/sodium citrate (SSC) at about 45° C., followed by a wash of 2.0×SSC at 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

Isolated and purified nucleic acid molecules having sequences which differ from the nucleic acid sequence shown in SEQ.ID.NO.:1 or SEQ.ID.NO.:3 or SEQ.ID.NO.:5 due to degeneracy in the genetic code are also within the scope of the invention.

Nucleic acid molecules from the EPM2A gene can be isolated by preparing a labelled nucleic acid probe based on all or part of the nucleic acid sequences as shown in SEQ.ID.NO.:1 and FIG. 13, and using this labelled nucleic acid probe to screen an appropriate DNA library (e.g. a CDNA or genomic DNA library). Nucleic acids isolated by screening of a cDNA or genomic DNA library can be sequenced by standard techniques.

Nucleic acid molecules of the invention can also be isolated by selectively amplifying a nucleic acid using the polymerase chain reaction (PCR) methods and cDNA or genomic DNA. It is possible to design synthetic oligonucleotide primers from the nucleic acid molecules as shown in SEQ.ID.NO.:1 and FIG. 13, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St Petersburg, Fla.).

An isolated nucleic acid molecule of the invention which is RNA can be isolated by cloning a cDNA encoding a novel protein of the invention into an appropriate vector which allows for transcription of the cDNA to produce an RNA molecule which encodes the Laforin protein. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

The initiation codon and untranslated sequences of the nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule. Preferably, an antisense sequence is constructed by inverting a region preceding the initiation codon or an unconserved region. In particular, the nucleic acid sequences contained in the nucleic acid molecules of the invention or a fragment thereof, preferably a nucleic acid sequence shown in SEQ.ID.NO.:1, SEQ.ID.NO.:3 or SEQ.ID.NO.:5 may be inverted relative to its normal presentation for transcription to produce antisense nucleic acid molecules.

The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The invention also provides nucleic acids encoding fusion proteins comprising a novel protein of the invention and a selected protein, or a selectable marker protein (see below).

II. Novel Proteins of the Invention

The invention further includes an isolated protein encoded by the nucleic acid molecules of the invention. Within the context of the present invention, a protein of the invention may include various structural forms of the primary protein which retain biological activity.

Broadly stated, the present invention provides an isolated protein containing a tyrosine phosphatase domain and which is associated with Lafora's disease.

In a preferred embodiment of the invention, the protein has the amino acid sequence as shown in SEQ ID NO:2 and FIG. 14. In another embodiment, the protein has the amino acid sequence shown in SEQ.ID.NO.:4 (or FIG. 8) or SEQ.ID.NO.:6 (or FIG. 10).

In addition to full length amino acid sequences the proteins of the present invention also include truncations of the protein, and analogs, and homologs of the protein and truncations thereof as described herein. Truncated proteins may comprise peptides of at least fifteen amino acid residues.

Analogs of the protein having the amino acid sequence shown in SEQ.ID.NO.:2 (FIG. 14) or SEQ.ID.NO.:4 (FIG. 8) or SEQ.ID.NO.:6 (FIG. 10) and/or truncations thereof as described herein, may include, but are not limited to an amino acid sequence containing one or more amino acid substitutions, insertions, and/or deletions. Amino acid substitutions may be of a conserved or non-conserved nature. Conserved amino acid substitutions involve replacing one or more amino acids of the proteins of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the ammio acid sequences shown in SEQ.ID.NO.:2 (FIG. 14) or SEQ.ID.NO.:4 (FIG. 8) or SEQ.ID.NO.:6 (FIG. 10). Amino acid insertions may consist of single amino acid residues or sequential amino acids ranging from 2 to 15 amino acids in length. For example, amino acid insertions may be used to destroy target sequences so that the protein is no longer active. This procedure may be used in vivo to inhibit the activity of a protein of the invention.

Deletions may consist of the removal of one or more amino acids, or discrete portions from the amino acid sequence shown in SEQ.ID.NO.:2 (FIG. 14) or SEQ.ID.NO.:4 (FIG. 8) or SEQ.ID.NO.:6 (FIG. 10). The deleted amino acids may or may not be contiguous. The lower limit length of the resulting analog with a deletion mutation is about 10 amino acids, preferably 100 amino acids.

Analogs of a protein of the invention may be prepared by introducing mutations in the nucleotide sequence encoding the protein. Mutations in nucleotide sequences constructed for expression of analogs of a protein of the invention must preserve the reading frame of the coding sequences. Furthermore, the mutations will preferably not create complementary regions that could hybridize to produce secondary mRNA structures, such as loops or hairpins, which could adversely affect translation of the receptor mRNA.

Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site specific mutagenesis procedures may be employed to provide an altered gene having particular codons altered according to the substitution, deletion, or insertion required. Deletion or truncation of a protein of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The proteins of the invention also include homologs of the amino acid sequence shown in SEQ.ID.NO.:2 (FIG. 14) or SEQ.ID.NO.:4 (FIG. 8) or SEQ.ID.NO.:6 (FIG. 10) and/or truncations thereof as described herein. Such homologs are proteins whose amino acid sequences are comprised of amino acid sequences that hybridize under stringent hybridization conditions (see discussion of stringent hybridization conditions herein) with a probe used to obtain a protein of the invention. Preferably, homologs of a protein of the invention will have a tyrosine phosphatase region which is characteristic of the protein.

A homologous protein includes a protein with an amino acid sequence having at least 70%, preferably 80–90% identity with the amino acid sequence as shown in SEQ.ID.NO.:2 (FIG. 14) or SEQ.ID.NO.:4 (FIG. 8) or SEQ.ID.NO.:6 (FIG. 10).

The invention also contemplates isoforms of the proteins of the invention. An isoform contains the same number and kinds of amino acids as a protein of the invention, but the isoform has a different molecular structure. The isoforms contemplated by the present invention are those having the same properties as a protein of the invention as described herein.

The present invention also includes a protein of the invention conjugated with a selected protein, or a selectable marker protein (see below) to produce fusion proteins. Additionally, immunogenic portions of a protein of the invention are within the scope of the invention.

The proteins of the invention (including truncations, analogs, etc.) may be prepared using recombinant DNA methods. Accordingly, the nucleic acid molecules of the present invention having a sequence which encodes a protein of the invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, or viral genes (For example, see the regulatory; sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

The invention further provides a recombinant expression vector comprising a DNA nucleic acid molecule of the invention cloned into the expression vector in an antisense orientation That is, the DNA molecule is operatively linked to a regulatory sequence in a manner which allows for expression, by transcription of the DNA molecule, of an RNA molecule which is antisense to a nucleotide sequence comprising the nucleotides as shown SEQ.ID.NO.:1, SEQ.ID.NO.:3 or SEQ.ID.NO.:5. Regulatory sequences operatively linked to the antisense nucleic acid can be chosen which direct the continuous expression of the antisense RNA molecule.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of a target recombinant protein by acting as a ligand in affinity purification. For example, a proteolytic cleavage site may be added to the target recombinant protein to allow separation of the recombinant protein from the fusion moiety subsequent to purification of the fusion protein.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as E. coli, insect cells (using baculovirus), yeast cells or mammalian cells. Other suitable host cells can be found in Goeddel, Gene Expression Technology: Methods in Enzymology 185, Academic Press, San Diego, Calif. (1991).

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

III. Applications

A. Diagnostic Applications

As previously mentioned, the present inventors have isolated and sequenced a novel gene EPM2A and have shown that it is deleted or mutated in people with Lafora's disease. As a result, the present invention also includes a method of detecting Lafora's disease by detecting a mutation or deletion in the Lafora's disease gene or protein.

i) Detecting Mutations in the Nucleic Acid Sequence

In one embodiment, the present invention provides a method for detecting Lafora's disease comprising detecting a deletion or mutation in the Lafora's disease gene in a sample obtained from an animal, preferably a mammal, more preferably a human. Preferably, the invention provides a method of detecting Lafora's disease comprising detecting a deletion or mutation in the Lafora's disease gene in the region between markers D6S1003 and D6S1042.

The Examples and Tables 1 to 3 summarize some of the mutations found in EPM2A in patient's with Lafora's Disease. Screening assays can be developed for each of the mutations. Details of screening assays that may be employed for the 3 common mutations are provided in Example 3.

One of the common EPM2A mutations is a C→T nonsense mutation of the second base pair of exon 4 found at position 721 in FIG. 13. This mutation destroys the recognition site for the restriction enzyme HaeIII. Accordingly, the C to T mutation can be detected in a sample by a method comprising:

(a) amplifying the nucleic acid sequences in the sample with primers H1F (5'-GAATGCTCTTTCCACTTTGC-3) (SEQ ID NO: 7) and PTPR (5'-GGCTCCTTAGGGAAATCAG-3') (SEQ ID NO: 8) in a polymerase chain reaction;

(b) digesting the amplified sequences with the restriction endonuclease HaeIII; and (c) determining the size of the digested sequences wherein the presence of a fragment of approximately 199 bp indicates the sample is from an animal with Lafora's disease or an animal that is a carrier of Lafora's disease.

Another common mutation in EMP2A is a G→A mutation of base pair 115 in exon 4 (position 836 in FIG. 13). This mutation creates a new PstI restriction site in the 520 bp DNA fragment that is amplified by primers H1F and PTPR, which is not found in normal, non-carrier individuals. Consequently, the present invention provides a method for detecting a G to A mutation in EMP2A by a method comprising:

(a) amplifying the nucleic acid sequences in the sample with primers H1F (5'-GAATGCTCTTTCCACTTTGC-3) (SEQ ID NO: 7) and PTPR (5'-GGCTCCTTAGGGAAATCAG-3') (SEQ ID NO: 8) in a polymerase chain reaction;

(b) digesting the amplified sequences with the restriction endonuclease Pst1; and (c) determining the size of the digested sequences wherein the presence of at least one fragment of approximately 520 bp indicates that the sample is from an animal that does not have Lafora's disease or an animal that is a carrier of Lafora's disease. Persons with Lafora's disease will have two variant bands of 195 base pairs and 350 base pairs.

Many families with Lafora's disease have deletions of EPM2A. Patients homozygous for these deletions can be detected by the absence of PCR amplification products using primers JRGXBF/JRGXBR which amplify the deleted region. Consequently, the present invention includes a method for determining a deletion in the EMP2A gene by a method comprising:

(a) amplifying the nucleic acid sequences in the sample with primers JRGXBF (5'-TCCATTGTGCTAATGCTATCTC-3') (SEQ ID NO: 9) and JRGXBR (5'-TCAGCTTGCTTTGAGGATATTT-3') (SEQ ID NO: 10) in a polymerase chain reaction; and (b) detecting amplified sequence wherein the absence of an amplified sequence indicates that the sample is from an animal with Lafora's disease.

One skilled in the art will appreciate that other methods, in addition to the ones discussed above and in the examples, can be used to detect mutations in the EPM2A gene. For example, in order to isolate nucleic acids from the Lafora's disease gene in a sample, one can prepare nucleotide probes from the nucleic acid sequences of the invention. In addition, the nucleic acid probes described herein (for example, see FIG. 1) can also be used. A nucleotide probe may be labelled with a detectable marker such as a radioactive label which provides for an adequate signal and has sufficient half life such as $^{32}P$, $^{3}H$, $^{14}C$ or the like. Other detectable markers which may be used include antigens that are recognized by a specific labelled antibody, fluorescent compounds, enzymes, antibodies specific for a labelled antigen, and chemiluminescent compounds. An appropriate label may be selected having regard to the rate of hybridization and binding of the probe to the nucleotide to be detected and the amount of nucleotide available for hybridization.

Accordingly, the present invention also relates to a method of detecting the presence of a nucleic acid molecule from the EPM2A gene in a sample comprising contacting the sample under hybridization conditions with one or more of nucleotide probes which hybridize to the nucleic acid molecules and are labelled with a detectable marker, and determining the degree of hybridization between the nucleic acid molecule in the sample and the nucleotide probes. Preferably, the nucleic acid probes hybridize with a portion of the EPM2A gene containing a mutation site in Lafora's disease, for example, in the region between marker DS61003 and DS61042.

Hybridization conditions which may be used in the methods of the invention are known in the art and are described for example in Sambrook J, Fritch E F, Maniatis T. In: Molecular Cloning, A Laboratory Manual,1989. (Nolan C, Ed.), Cold Spring Harbor Laboratory Press, Cold Spring Harbor, N.Y. The hybridization product may be assayed using techniques known in the art. The nucleotide probe may be labelled with a detectable marker as described herein and the hybridization product may be assayed by detecting the detectable marker or the detectable change produced by the detectable marker.

Prior to hybridizing a sample with DNA probes, the sample can be treated with primers that flank the EPM2A gene in order to amplify the nucleic acid sequences in the sample. The primers used may be the ones described in the present application. For example, primers specific for the transcript A include 266F and GSP3. Primers for the transcript B include AA490925F and AA490925R. In addition, the sequence of the EPM2A gene provided herein also permits the identification and isolation, or synthesis of new nucleotide sequences which may be used as primers to amplify a nucleic acid molecule of the invention, for example in the polymerase chain reaction (PCR) which is discussed in more detail below. The primers may be used to amplify the genomic DNA of other species. The PCR amplified sequences can be examined to determine the relationship between the genes of various species.

The length and bases of the primers for use in the PCR are selected so that they will hybridize to different strands of the desired sequence and at relative positions along the sequence such that an extension product synthesized from one primer when it is separated from its template can serve as a template for extension of the other primer into a nucleic acid of defined length. Primers which may be used in the invention are oligonucleotides i.e. molecules containing two or more deoxyribonucleotides of the nucleic acid molecule of the invention which occur naturally as in a purified restriction endonuclease digest or are produced synthetically using techniques known in the art such as for example phosphotriester and phosphodiester methods (See Good et al Nucl. Acid Res 4:2157, 1977) or automated techniques (See for example, Conolly, B. A. Nucleic Acids Res. 15:15(7): 3131, 1987). The primers are capable of acting as a point of initiation of synthesis when placed under conditions which permit the synthesis of a primer extension product which is complementary to the DNA sequence of the invention i.e. in the presence of nucleotide substrates, an agent for polymerization such as DNA polymerase and at suitable temperature and pH. Preferably, the primers are sequences that do not form secondary structures by base pairing with other copies of the primer or sequences that form a hair pin configuration. The primer preferably contains between about 7 and 25 nucleotides.

The primers may be labelled with detectable markers which allow for detection of the amplified products. Suitable detectable markers are radioactive markers such as P-32, S-35, I-125, and H-3, luminescent markers such as chemiluminescent markers, preferably luminol, and fluorescent markers, preferably dansyl, chloride, fluorcein-5-isothiocyanate, and 4-fluor-7-nitrobenz-2-axa-1,3 diazole, enzyme markers such as horseradish peroxidase, alkaline phosphatase, β-galactosidase, acetylcholinesterase, or biotin.

It will be appreciated that the primers may contain non-complementary sequences provided that a sufficient amount of the primer contains a sequence which is complementary to a nucleic acid molecule of the invention or oligonucleotide fragment thereof, which is to be amplified. Restriction site linkers may also be incorporated into the primers allowing for digestion of the amplified products with the appropriate restriction enzymes facilitating cloning and sequencing of the amplified product.

In an embodiment of the invention a method of determining the presence of a nucleic acid molecule of the invention is provided comprising treating the sample with primers which are capable of amplifying the nucleic acid molecule or a predetermined oligonucleotide fragment thereof in a polymerase chain reaction to form, amplified sequences, under conditions which permit the formation of amplified sequences and, assaying for amplified sequences.

The polymerase chain reaction refers to a process for amplifying a target nucleic acid sequence as generally described in Innis et al, Academic Press, 1990 in Mullis el al., U.S. Pat. No. 4,863,195 and Mullis, U.S. Pat. No. 4,683,202 which are incorporated herein by reference. Conditions for amplifying a nucleic acid template are described in M. A. Innis and D. H. Gelfand, PCR Protocols, A Guide to Methods and Applications M. A. Innis, D. H. Gelfand, J. J. Sninsky and T. J. White eds, pp3–12, Academic Press 1989, which is also incorporated herein by reference.

The amplified products can be isolated and distinguished based on their respective sizes using techniques known in the art. For example, after amplification, the DNA sample can be separated on an agarose gel and visualized, after staining with ethidium bromide, under ultra violet (UW) light. DNA may be amplified to a desired level and a further extension reaction may be performed to incorporate nucleotide derivatives having detectable markers such as radioactive labelled or biotin labelled nucleoside triphosphates. The primers may also be labelled with detectable markers as discussed above. The detectable markers may be analyzed by restriction and electrophoretic separation or other techniques known in the art.

The conditions which may be employed in the methods of the invention using PCR are those which permit hybridization and amplification reactions to proceed in the presence of DNA in a sample and appropriate complementary hybridization primers. Conditions suitable for the polymerase chain reaction are generally known in the art. For example, see M. A. Innis and D. H. Gelfand, PCR Protocols, A guide to Methods and Applications M. A. Innis, D. H. Gelfand, J. J. Sninsky and T. J. White eds, pp3–12, Academic Press 1989, which is incorporated herein by reference. Preferably, the PCR utilizes polymerase obtained from the thermophilic bacterium Thermus aquatics (Taq polymerase, GeneAmp Kit, Perkin Elmer Cetus) or other thermostable polymerase may be used to amplify DNA template strands.

It will be appreciated that other techniques such as the Ligase Chain Reaction (LCR) and NASBA may be used to amplify a nucleic acid molecule of the invention (Barney in "PCR Methods and Applications", August 1991, Vol.1(1), page 5, and European Published Application No. 0320308, published Jun. 14, 1989, and U.S. Ser. No. 5,130,238 to Malek).

(ii) Detecting the Laforin Protein

In another embodiment, the present invention provides a method for detecting Lafora's disease comprising determining if the Laforin protein is present in a sample from an animal.

The Laforin protein of the present invention may be detected in a biological sample using antibodies that are specific for Laforin using various immunoassays that are discussed below.

Conventional methods can be used to prepare the antibodies. For example, by using a peptide from the Laforin protein of the invention, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246,1275 (1989)]. Hybridoma cells can be screened immunochemnically for production of antibodies specifically reactive with the peptide and the monoclonal antibodies can be isolated. Therefore, the invention also contemplates hybridoma cells secreting monoclonal antibodies with specificity for a protein of the invention.

The term "antibody" as used herein is intended to include fragments thereof which also specifically react with a protein, of the invention, or peptide thereof. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a CipA protein (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B).

Monoclonal or chimeric antibodies specifically reactive with a protein of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A, 80, 7308–7312 (1983); Kozbor et al., Immunology Today, 4, 7279 (1983); Olsson et al., Meth. Enzymol., 92, 3–16 (1982)), and PCT Publication W092/06193 or EP 0239400). Humanized antibodies can also be commercially produced (Scotgen Limited, 2 Holly Road, Twickenham, Middlesex, Great Britain.)

Specific antibodies, or antibody fragments, reactive against a protein of the invention may also be generated by screening expression libraries encoding immunoglobulin genes, or portions thereof, expressed in bacteria with peptides produced from the nucleic acid molecules of the present invention. For example, complete Fab fragments, VH regions and FV regions can be expressed in bacteria using phage expression libraries (See for example Ward et al., Nature 341, 544–546: (1989); Huse et al., Science 246, 1275–1281 (1989); and McCafferty et al. Nature 348, 552–554 (1990)).

Antibodies may also be prepared using DNA immunization. For example, an expression vector containing a nucleic acid of the invention (as described above) may be injected into a suitable animal such as mouse. The protein of the invention will therefore be expressed in vivo and antibodies will be induced. The antibodies can be isolated and prepared as described above for protein immunization.

The antibodies may be labelled with a detectable marker including various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include S35, Cu64, Ga67, Zr-89, Ru-97, Tc-99m, Rh-105, Pd-109, In-111, I-123, I-125, I-131, Re-186, Au-198, Au-199, Pb-203, At-211, Pb-212 and Bi-212. The antibodies may also be labelled or conjugated to one partner of a ligand binding pair. Representative examples include avidin-biotin and riboflavin-riboflavin binding protein. Methods for conjugating or labelling the antibodies discussed above with the representative labels set forth above may be readily accomplished using conventional techniques.

The antibodies reactive against proteins of the invention (e.g. enzyme conjugates or labelled derivatives) may be used to detect a protein of the invention in various samples, for example they may be used in any known immunoassays which rely on the binding interaction between an antigenic determinant of a protein of the invention and the antibodies. Examples of such assays are radioimmunoassays, enzyme immunoassays (e.g. ELISA), immunofluorescence, immuno-precipitation, latex agglutination, hemagglutination, and histochemical tests. Thus, the antibodies may be used to identify or quantify the amount of a protein of the invention in a sample in order to diagnose the presence of Lafora's disease.

In a method of the invention a predetermined amount of a sample or concentrated sample is mixed with antibody or labelled antibody. The amount of antibody used in the process is dependent upon the labelling agent chosen. The resulting protein bound to antibody or labelled antibody may be isolated by conventional isolation techniques, for example, salting out, chromatography, electrophoresis, gel filtration, fractionation, absorption, polyacrylamide gel electrophoresis, agglutination, or combinations thereof.

The sample or antibody may be insolubilized, for example, the sample or antibody can be reacted using known methods with a suitable carrier. Examples of suitable carriers are Sepharose or agarose beads. When an insolubilized sample or antibody is used protein bound to antibody or unreacted antibody is isolated by washing. For example, when the sample is blotted onto a nitrocellulose membrane, the antibody bound to a protein of the invention is separated from the unreacted antibody by washing with a buffer, for example, phosphate buffered saline (PBS) with bovine serum albumin (BSA).

When labelled antibody is used, the presence of Laforin can be determined by measuring the amount of labelled antibody bound to a protein of the invention in the sample or of the unreacted labelled antibody. The appropriate method of measuring the labelled material is dependent upon the labelling agent.

When unlabelled antibody is used in the method of the invention, the presence of Laforin can be determined by measuring the amount of antibody bound to the protein using substances that interact specifically with the antibody to cause agglutination or precipitation. In particular, labelled antibody against an antibody specific for a protein of the invention, can be added to the reaction mixture. The presence of a protein of the invention can be determined by a suitable method from among the already described techniques depending on the type of labelling agent The antibody against an antibody specific for a protein of the invention can be prepared and labelled by conventional procedures known in the art which have been described herein. The antibody against an antibody specific for a protein of the invention may be a species specific anti-immunoglobulin antibody or monoclonal antibody, for example, goat anti-rabbit antibody may be used to detect rabbit antibody specific for a protein of the invention.

(iii) Kits

The reagents suitable for carrying out the methods of the invention may be packaged into convenient kits providing the necessary materials, packaged into suitable containers. Such kits may include all the reagents required to detect a nucleic acid molecule or protein of the invention in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment thereof in the polymerase chain reaction, and means for assaying the amplified sequences. The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention the kit includes antibodies of the invention and reagents required for binding of the antibody to a protein of the invention in a sample.

The methods and kits of the present invention may be used to detect Lafora's disease. Samples which may be tested include bodily materials such as blood, urine, serum, tears, saliva, feces, tissues, cells and the like. In addition to human samples, samples may be taken from mammals such as non-human primates, etc.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

B. Therapeutic Applications

As mentioned previously, the nucleic add molecules of the present invention are deleted or mutated in people with Lafora's disease. Accordingly, the present invention provides a method of treating or preventing Lafora's disease by administering a nucleic acid sequence containing a sufficient portion of the EPM2A gene to treat or prevent Lafora's disease.

Recombinant molecules comprising a nucleic acid sequence or fragment thereof, may be directly introduced into cells or tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes. Recombinant molecules may also be delivered in the form of an aerosol or by lavage.

The nucleic acid sequences may be formulated into pharmaceutical compositions for adminstration to subjects in a biologically compatible form suitable for administration in vivo. By "biologically compatible form suitable for administration in vivo", is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima tray be adjusted to provide the optimum therapeutic response. For example, several divided doses may be administered daily or the dose may be proportionally reduced as indicated by the exigencies of the therapeutic situation.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

C. Experimental Models

The present invention also includes methods and experimental models for studying the function of the EPM2A gene and Laforin protein. Cells, tissues and non-human animals that lack the EPM2A gene or partially lack in Laforin expression may be developed using recombinant expression vectors having a specific deletion or mutation in the EPM2A gene. A recombinant expression vector may be used to inactivate or alter the EPM2A gene by homologous recombination and thereby create an EPM2A deficient cell, tissue or animal.

Null alleles may be generated in cells, such as embryonic stem cells by deletion mutation. A recombinant EPM2A gene may also be engineered to contain an insertion mutation which inactivates EPM2A. Such a construct may then be introduced into a cell, such as an embryonic stem cell, by a technique such as transfection, electroporation, injection etc. Cells lacking an intact EPM2A gene may then be identified, for example by Southern blotting Northern Blotting or by assaying for EPM2A using the methods described herein. Such cells may then be fused to embryonic stem cells to generate transgenic non-human animals deficient in EPM2A. Germline transmission of the mutation may be achieved, for example, by aggregating the embryonic stem cells with early stage embryos, such as 8 cell embryos, in vitro; transferring the resulting blastocysts into recipient females and; generating germline transmission of the resulting aggregation chimeras. Such a mutant animal may be used to define specific cell populations, developmental patterns and in vivo processes, normally dependent on EPM2A expression. The present invention also includes the preparation of tissue specific knock-outs of the EPM2A gene.

The following non-limiting examples are illustrative of the present invention:

EXAMPLES

Example 1

Characterization of EPM2A

Materials and Methods

Patients. The diagnosis of Lafora's disease in patients with teenage onset progressive myoclonus epilepsy was confirmed by demonstration of Lafora bodies in skin, liver, muscle or brain biopsies (6–9) in at least one affected member from each of 38 families included in this study.

Physical mapping. Using mapping data available from the Whitehead Institute/MIT Genome Center (http://mit-genome.wi.mit.edu/) as well as by identifying additional clones it was possible to establish an overlapping set of yeast artificial chromosome (YAC) clones between D6S1003 and D6S311. A total of 136 markers (12 genes, 41 ESTs, and 83 STSs/probes) were assayed against the YAC contig and 32 of these were found to be in the EPM2A critical region (FIG. 1). We also isolated 129 P1-derived artificial chromosomes (PACs) which cover an estimated 90% of the region between D6S1003 and D6S311 and have aligned the PACs by probe content, restriction mapping, as well fingerprint analysis. Information on all DNA markers can be found at the Genome DataBase (http://www.gdbwww.gdb.org/) or the Sanger Genome Center WWW site (http://www.sanger.ac.uk/HGP/Chr6/).

FIG. 1 illustrates the physical map of the Lafora's disease critical region. (A). A yeast artificial chromosome (YAC) contig was established covering the 1.5 Mb critical region between D6S1003 and D6S311. The presence of a DNA marker on a YAC clone is shown by a corresponding vertical bar. The markers that are highlighted with a circle and a square represent genetic markers or ESTs, respectively, while the raining ones are unique landmarks (STSs). The region between D6S1003 and D6S1042 that demonstrated an extended region of homozygosity in affected members of a previously uncharacterized family is shown by a thicker horizontal bar and this is the new EPM2A critical region (see FIG. 2A); (B). A P1-derived artificial chromosome (PAC) map encompassing the immediate region surround D6S1703. The extent of the deletion could be defined by PCR analysis of mapped STSs (see FIG. 2B). LDCR4 represents a transcript of unidentified function and EPM2A is the Lafora disease gene. Since the 5'-end of this gene is not yet known it is represented with a dashed line.

Figure 3:
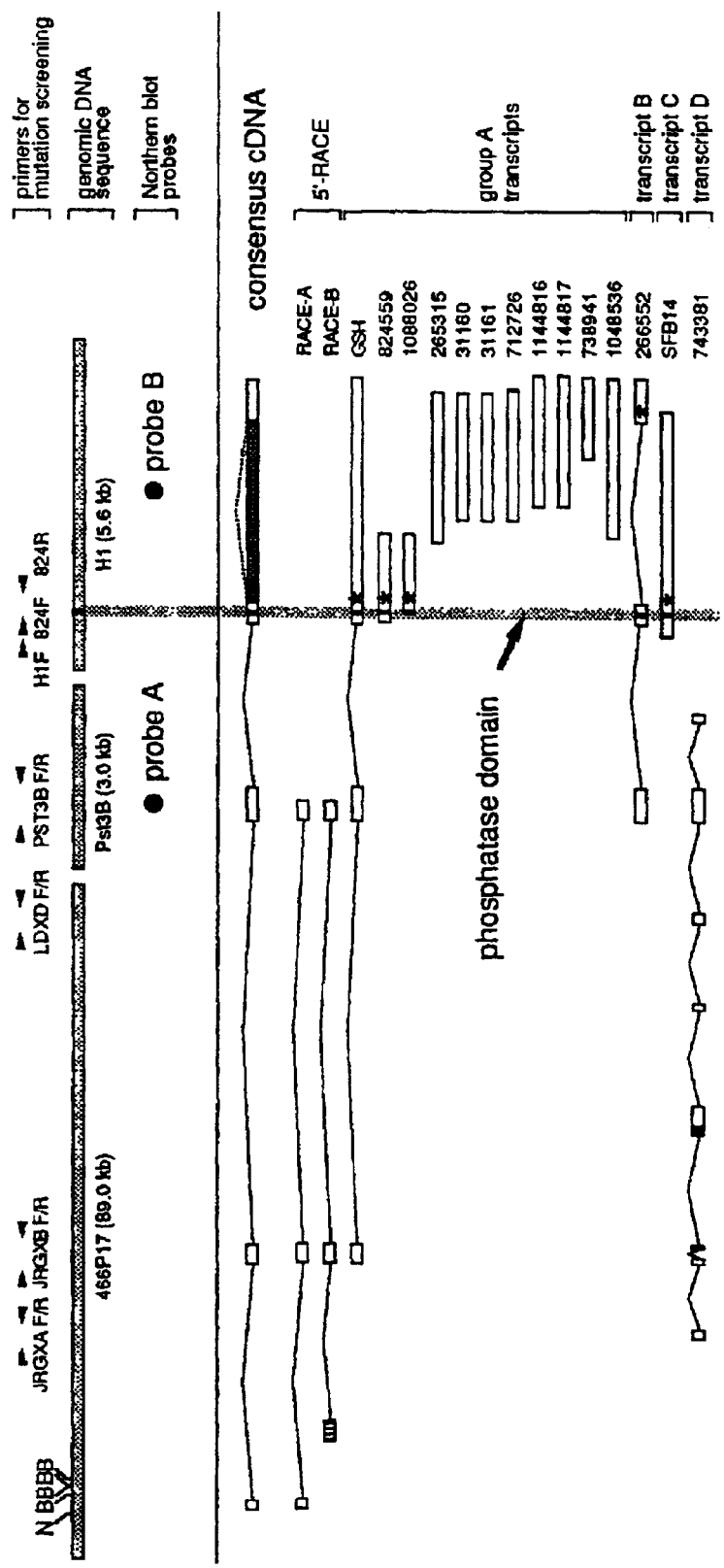
FIG. 3 shows overlapping cDNA clones aligned with genomic DNA segments.

Northern blots, cDNA library screening, and RACE. Multiple-tissue (cat. #7760-1) and Human Brain II (cat. #7755-1) Northern blots were purchased from Clontech and hybridization was carried out as recommended by the supplier. The transcript A specific probe was generated using PCR primers 266F (SEQ ID NO: 11) (5'-CGGCACGAGGATTATTCAAG-3') and GSP3 (5'-GCTCGGGTACTGAGGTCTG-3') (SEQ ID NO: 12) which amplified an 190 bp fragment from cDNA clone 266552; (FIG. 3). The transcript B specific probe was derived using PCR primers AA490925F (5'-AGTTGTTACACAGGGTTGTTGG-3') (SEQ ID NO: 13) and AA490925R (5'-AGGCTGTACATCAGACAGAAGG-3') (SEQ ID NO: 14) which amplified an 373 bp segment from cDNA SFB14 (FIG. 3). We have sequenced the HTF-island shown in FIG. 1B at the 5'-end of EPM2A.

Genotyping. Haplotypes for 6q23-25 were constructed for all family members using microsatellite markers at loci D6S314, D6S1704, D6S1003, D6S1010, D6S1049, D6S1703, D6S1042, D6S1649, D6S978, D6S311 and D6S1637. Primer sequences from Genethon or from the Cooperative Human Linkage Centre. PCR conditions have been reported previously (13). PCR products were separated on polyacrylamide gels. In 8 families (20%), haplotype analyses revealed evidence against linkage to 6q23-25. Of the remaining 30 LD families 16 reported a history of consanguinity Thirty-one of these families have been described previously (refs. 12, 13, 25, 25).

Mutation Analysis. Mutations were detected by radioactive cycle sequencing using the Thermosequenase Kit (Amersham Life Science) with Qiagen column purified PCR products. The combinations of PCR primer pairs used were JRGXBCF (5'-TCCATTGTGCTAATGCTATCTC-3') (SEQ ID NO: 15) and JRGXBCR (SEQ ID NO: 16) (5'-TCAGCTTGCTTTGAGGATATTT-3'); product size 310 bp, 824F (5'-GCCGAGTACAGATGCTGCC-3' (SEQ ID NO: 17) and 824R (SEQ ID NO: 18) (5'-CACACAGTCCTTTCAGTTCAGG-3'); product size 384 bp, and H1F (5'-GAATCTCTTTCCACTTTGC-3' (SEQ ID NO: 7) and 824R; product size 587 bp. The position of the primers are shown in FIG. 3.

Characterization of Lafora's Disease Gene To characterize the extent of the homozygous deletion in the affected in LD-L4 a P1-derived artificial chromosome (PAC) contig extending outwards from D6S1703 was constructed. It could be determined that the deletion encompassed approximately 50 kb and that it did not interrupt directly the LDCR4 transcription unit (FIG. 1B). PAC clones 365C1, 466P17 and 28H5 (which encompassed the deletion) were sequenced in order to identify new candidate transcription units (FIG. 1B). A segment of DNA (E42) located within the deletion detected a single EST (done 743381) in the database (FIG. 3). DNA sequencing of this cDNA indicated it contained a segment of identity with one other EST (266552). This EST, however, was aligned previously with others into separate groups (or Unigenes named Hs.22464 and Hs.112229). Subsequently, we used clone 743381 and 824559 and PCR primers derived from their sequence for screening of multiple cDNA libraries in an attempt to clone the entire coding region of this gene.

Figure 2:
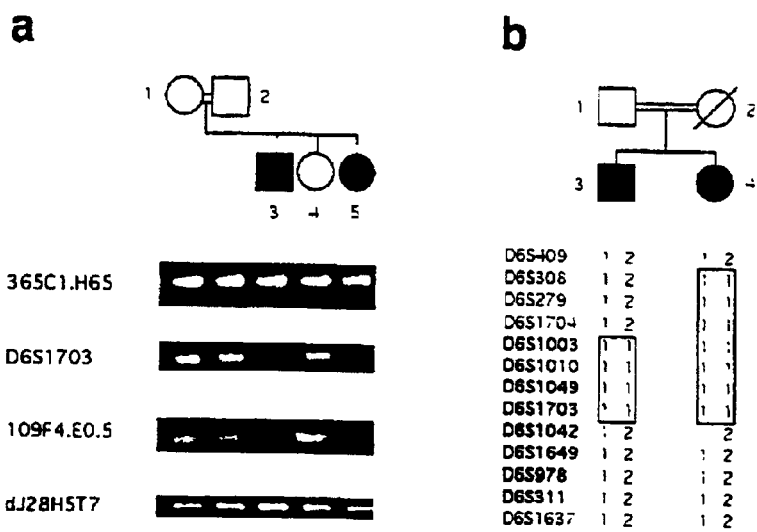
FIG. 2A shows a refined mapping of the Lafora disease gene for Lafora family LD39.
FIG. 2B is for Lafora family LD-L4.

FIG. 2 shows a refined mapping of the Lafora disease gene. (A) Pedigrees and genotype data are provided for Lafora family LD39. Individuals affected (solid) or unaffected (open) with Lafora disease are indicated. Below each individual is the corresponding genotype data (the markers are listed in their order from centromere (top) to telomere (bottom) as determined using the physical map shown in FIG. 1). The boxed segments of the haplotypes indicate regions of homozygosity. The loci in bold indicate the previous LD critical region. (B) Detection of 2 markers (D6S1703 and 109F4.E05.5) determined to be absent by PCR in the affected members of the consanguineous Lafora family LD-L4.

FIG. 3 shows overlapping cDNA clones aligned with genomic DNA segments. The portions of each cDNA clone for which there was sequence is represented with a box. The corresponding genomic fragments are shown as stippled boxes below. The clones preceded with an (E) and (H) represent EcoR1 and HindIII fragments, respectively. The positions of the primers used for mutation screening are shown as is the site of the phosphatase domain and the stop codon (*).

Through analysis of the alignment of the DNA sequences of all of the EST clones as well as the newly identified cDNAs, at least 4 putative types of transcripts that corresponded to EPM2A could be defined (named transcript A, B, C, and D (FIG. 3). The cDNAs grouped into transcript A could be categorized based on regions of sequence identity at their 3'-ends. A consensus sequence was compiled and it was found to be distributed amongst 4 exons spanning approximately 130 kb (FIGS. 1A and 3). A single cDNA (266552) representing transcript B shared exact identity with transcript A except for the omission of a 1,700 bp segment due to splicing (FIGS. 3 and 4). By comparing the corresponding genomic regions to the cDNAs a common origin for transcript A and B could be verified suggesting they are alternative forms of the same gene, the gene-products, of which, would be predictedto have unique carboxyl-terminal amino acid sequences (FIG. 4B).

FIG. 4shows the nucleotide sequence of cDNA encoding the EPM2A gene together with the predicted amino acid sequence. (A) The consensus nucleotide sequence was derived from the cDNA clones 266552, RACE-A, RACE-B, RACE-C, and RACE:-D shown in FIG. 3. The position of the mutations identified are indicated. The (*) indicates a stop mutation site and the position of 2 known splice junctions is shown by the horizontal arrows. An A to T polymorphism which is present in approximately 40–50% of the population is shown; (B) the deduced C terminus of transcript A compared with transcript B. The latter arises due to the removal by splicing of nt 738–2508 (FIG. 3 and FIG. 4A), which would be predicted to generate an isoform with a unique 3' end. At the present time, transcript B is known to extend to position 94 of the predicted amino acid sequence shown (FIG. 4A). Transcript C (cDNA SFB14) is described elsewhere (C), the putative PTP active sites of EPM2A, MTM1, PTEN, PTP18, dPTP61F and viral PTP. The shaded amino acids (C and R) represent catalytic residues. On the basis of sequence analysis alone, laforin predicts an intracellular PTP with dual specificity phosphatase activity.

The inventors determined a partial map (FIG. 3) and sequenced the corresponding genomic regions that contained nucleotide identity to these segments to prove their common origin. The results suggest that transcript A, B, C and D are indeed alternatively spliced forms of the same gene. The consensus sequence presently compiled for transcript A was distributed amongst at least 4 exons spanning greater than 50 kb while transcript B was represented as a contiguous segment of DNA. A single EST clone, 743381, which represents another alternatively spliced form that appeared to be most common to transcript A was also identified (FIG. 3A). It contained at least 8 exons (FIG. 3) but a significant open reading frame was not detected. The newly identified gene, EPM2A, which encodes Laforin, was the only one determined to be deleted in family LD-L4 (FIG. 1)

Two other single cDNA clones, SFB14 and 743381, which could represent additional alternative forms of EPM2A, were also identified (FIG. 3). SFB14 was contiguous to genomic DNA and identical to the 3'-end of transcript A except it's open reading frame (ORF) was predicted to extend 48 amino acids 5' into the last intron shown in FIG. 3. Clone 743381 contained 8 exons with appropriate exon-intron boundaries (FIG. 3) but its significance could not be assessed due to the lack of continuous open reading frame.

In addition to the essential cysteine and arginine residues found in all PTPs FIG. 4C), EPM2A contains an aspartic acid positioned 31 residues amino-terminal of the cysteine nucleophile. This amino acid is important for catalysis as it is located on a loop that undergoes conformational change when substrate is bound to enzyme.

Figure 5:
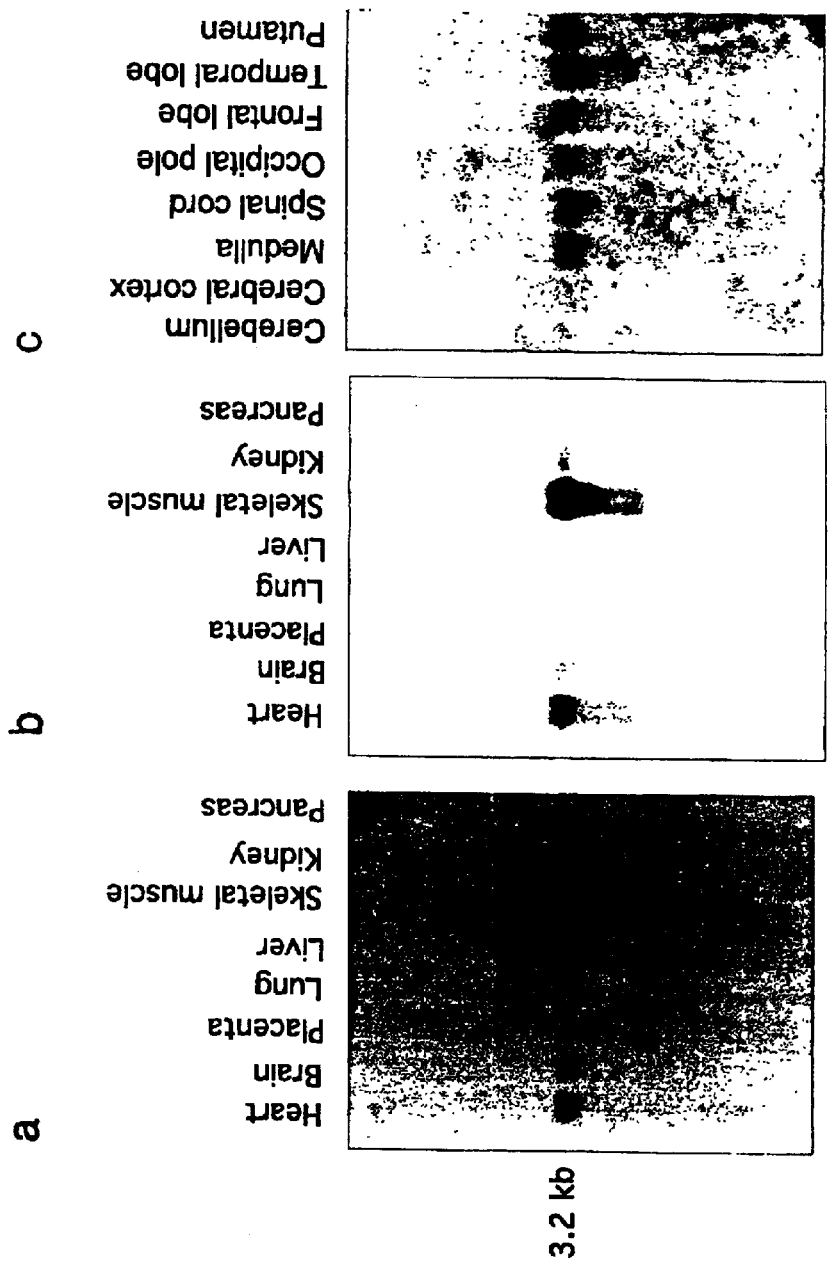
FIG. 5 is a Northern blot showing RNA expression pattern of EPM2A.

The corresponding mRNA for EPM2A was determined to be 3200 nucleotides in length in multiple tissues based on RNA gel-blot hybridization experiments. FIG. 5 shows RNA expression pattern of the Laforin gene. Northern blot analysis in different tissues as indicated at the top. The probes used are described in the Materials and Methods and the exposure time was 4 days at −80° C. The EPM2A message is observed in all tissues tested and the apparent overexpression in heart and skeletal muscle is due to overloading of mRNA in these lanes as was seen when using any gene-specific probe. The results of FIG. 5 illustrate that strong hybridization signals were detected in skeletal muscle RNA and clear signals were also seen in heart, brain, placenta, lung, liver, kidney and pancreas. In addition, the same size mRNA was detected in cerebellum, cerebral cortex, medulla, spinal cord, occipital pole, frontal lobe, temporal lobe, and putamen. Identical results showing the same 3200 nucleotide message and tissue distribution were observed when a DNA probe believed to be specific for each isoform of the gene based on the established consensus sequences, was used. For example, a probe derived from the 3'-UTR region of transcript B of EPM2A was determined unequivocally to be specific for this isoform. For transcript A, the probe was generated from the unique region shown in FIG. 4A and RT-PCR experiments seemed to confirm the specificity of this fragment (data not, shown). On the basis of northern-blot results and the relative number of ESTs identified, it is probable that transcript A represents the major isoform of EPM2A, and that it corresponds to the 3.2kb mRNA. From the analysis of the genomic DNA sequence, we have identified an additional ORF at the HTF-island (FIG. 3). As this predicted exon has all the proposed features of the consensus sequence of a eukaryotic translation initiation site, and 113 nt of it are represented in the consensus cDNA sequence, it could represent the 5' end of EPM2A.

The protein encoded by EPM2A contains an amino acid motif (FIG. 1C) that corresponds with the consensus sequence (SEQ ID NO: 22), HcxxGxxRS(T), of the catalytic site of PTPs. In addition to the essential cysteine and arginine residues found in all PTPs (FIG. 4C), EPM2A contains the expected aspartic acid necessary for completion of the catalytic reaction, positioned 31-aa N terminal of the cysteine nucleophile.

In an attempt to isolate the remainder of the coding region for these transcripts we performed multiple rounds of 5'-RACE on total brain and poly(A)+ mRNA which has allowed us to extend transcript A (but not transcript B) further. Beyond the most 5'-sequences shown in FIG. 4, however, all of the RACE clones recovered seemed to share the expected DNA sequences but then diverged in different ways that did not allow for a common consensus to be established. However, comparative DNA sequence analysis of the human EPM2A gene its corresponding mouse homolog (also called EPMA) confirmed the full length gene sequence as shown in FIG. 13.

The deduced amino acid sequence of the newly identified protein(s), indicated that transcripts A, B, C and D encode a 9 amino acid motif (FIG. 4A) that corresponds exactly to the consensus sequence (SEQ ID NO: 22), HCxxGxxRS(T), of the active catalytic site of protein tyrosine phosphatases (PTPs) (14,15). So far, no other structural motifs could be identified, and from the sequence it is not apparent if this protein belongs to the receptor-like PTPs, the intracellular PTPs, or the dual specificity phosphatases (DSPs) which dephosphorylate both tyrosine and serine/threonine residues (16). The identification of the EPM2A gene as a putative PTP provides the first clue to understand the basic defect.

At the HTF-island shown in FIG. 3, we have identified through GAIL analysis (http://compbio.ornl.gov) an additional putative exon 189 nucleotides in length. An ATG (AUG) triplet is present at the beginning of this predicted ORF and the nucleotide sequence (SEQ ID NO: 23) surrounding the consensus sequence (CCCGCCAUGC) has the proposed features of the consensus sequence (SEQ ID NO: 24) (GCCA/GCCAUGG) of a eukaryotic translation initiation site (12). The predicted start exon maintains open reading frame with the most 5' sequence of transcript A and this combined, stretch of 298 nucleotides contains exon/intron junction sequences with splice sites that confirm with the consensus in other mammalian genes. If the predicted axon is part of EPM2A, transcript A would be predicted to be 317 amino acids long.

Example 2
EPM2A Mutations

Using the available genomic structure for the gene, the inventors' screened an affected member from each of 30 Lafora families for mutations by direct DNA sequencing. A total of 14 mutations were detected consisting of 12 different DNA sequence alterations and 2 microdeletions. The mutations are summarized in Table 3. The mutation from C to A at position −12 refers to a mutation that occurs 12 bases upstream from the ATG start codon in FIG. 13. Some of the sequence upstream of the ATG is as follows: (SEQ ID NO: 19) . . . gccgggtattcgcgccgCcgccgcccgccATG . . . The mutation site at −12 is indicated with a capital C. To date, mutations have been found in 65% of EPM2A families. Some of the mutations are discussed below.

Two mutations that, based on the current consensus sequences were specific for transcript A, could be detected. Family LD-5 contained a homozygous C to T point mutation which resulted in an arginine to cysteine change affecting a region of unknown function. To test for the presence of the C to T point mutation in family LD-5 in the unaffected population PCR was completed on 54 samples (108 chromosomes) using JRGXBF and JRGXBR primers and the product was blotted in duplicate. One membrane was hybridized with a wild type oligonucleotide (ATCATGACCGTTGCTGTAC) (SEQ ID NO: 20) and the other with LD5 mutant (TCATCATGACTGTTGCTGTAC) (SEQ ID NO: 21) oligonucleotide at 42° C (washing with 5×SSC at room temperature for 20 minutes followed by 2×SSC 20 minutes at 65° C.). No mutant alleles were found.

The inventors have screened 100 normal chromosomes for this change and no mutant alleles were found. In family I-22 a homozygous G to T non-sense change in a region specific to transcript A would predict premature termination of the EPM2Av protein. In sequences common to both isoforms the inventors detected in the consanguineous family EPM2A00-4, a homozygous insertion of an A which would result in a frameshift that would cause an interruption of the tyrosine phosphatase domain. The inventors have identified in 4 consanguineous families a homozygous nonsense mutation which results from a C to T change which causes the introduction of a premature stop codon just preceding the tyrosine phosphatase domain. This same nonsense mutation was found on one chromosome of one additional family (L6) while the other chromosome had a G to A change resulting which results in a glycine to serine non-conservative substitution Finally, in family LD33 an A to T transition results in a glutamine to leucine change in a residue located just after the tyrosine phosphatase domain near the carboxy terminus. This mutation, apparently the mildest found, occurs in a family with relative preservation of mental functions and a relatively protracted course (13). The five families having the C to T change are all of Spanish decent indicating this may be the common mutation in this ethnic background.

Figure 6:
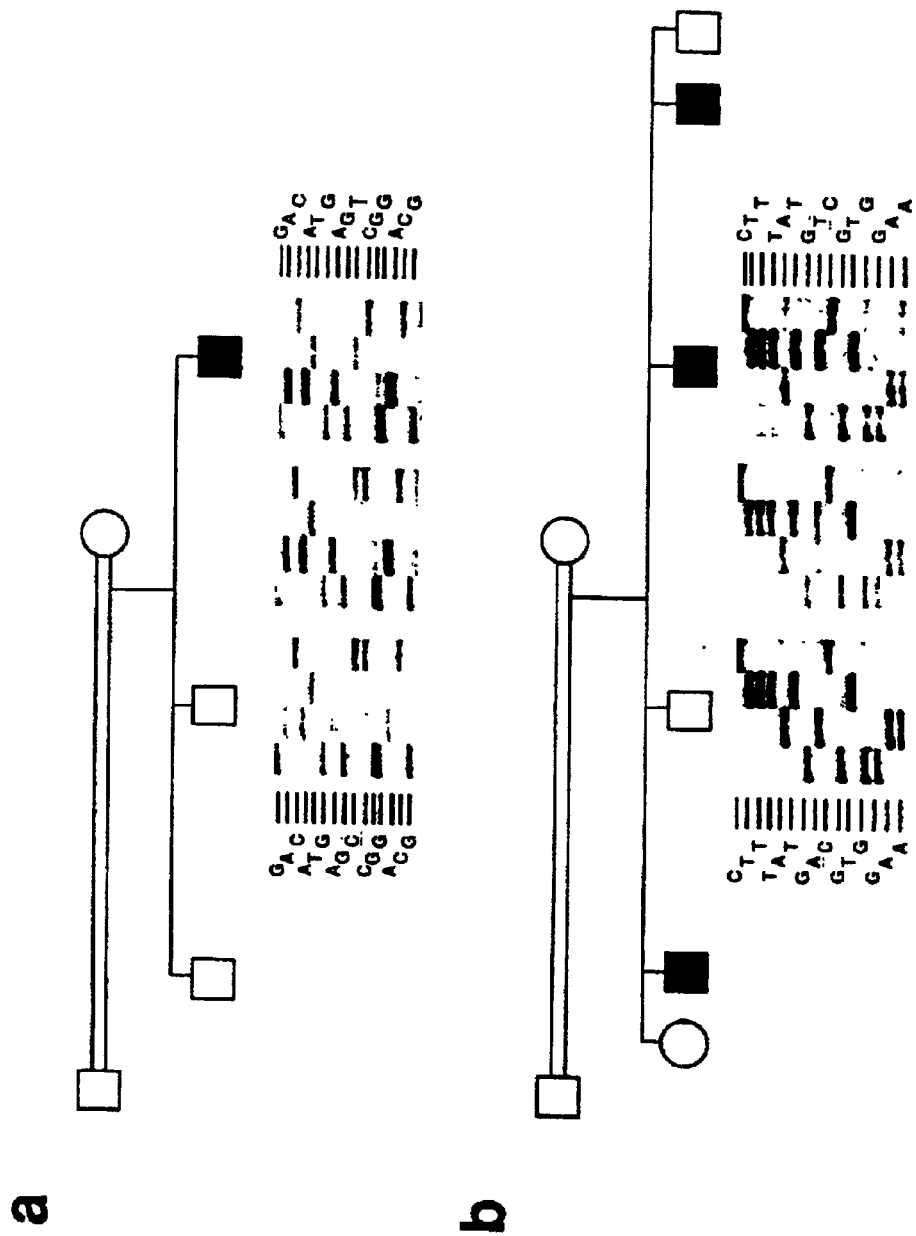
FIG. 6A shows representative mutations found in Lafora's family LD16.
FIG. 6B shows Lafora's family LD-33.

FIG. 6 shows representative mutations found in 2 Lafora's disease families. The left, middle, and right panels show the in-frame sequence of 5 codons surrounding an unaffected non-EPM2A carrier sibling, a EPM2A-carrier parent, and an affected EPM2A individual, respectively. (A) Family LD-16 in which a homozygous C to T transversion results in the introduction of a stop mutation, and (B) Family LD-33 in which a homozygous missense results in a glutamine to cysteine change.

The unraveling of the aetiopathogenesis of Lafora's disease needs to include an understanding of the formation of the pathognomonic Lafora bodies. These unique structures have been found in LD patients in the same tissues in which we have observed EPM2A expression (6–8, and FIG. 5). Polyglucosans are unbranched equivalents of glycogen (10). Polyglucosan bodies resembling and sharing common antigenicity with Lafora bodies have been found in glycogen storage disease type IV (Andersen disease) and in the normal corpora amylacea of aged brains (17). Andersen disease has been shown to arise due to mutations in the a-1,4 glucan gene on chromosome 3 which codes for the glycogen branching enzyme (18). It is possible that mutations in a gene that lead to the lack of production of the Laforin tyrosine phosphatase protein could affect the metabolism of glycogen. Both glycogen biosynthesis and breakdown are heavily regulated by phosphokinases and phosphatases (14).

EPM2A has at least two alternate forms (as does MTM1) which appear to encode protein isoforms that might be predicted to have different functions or subcellular localizations in a manner analagous to the Drosophila PTP, dPTP61F, which also undergoes alternative splicing at the 3' end (24 ,21). In the case of dPTP61F, it is known that the alternate carboxy termini govern the localization of the protein to either the cytoplasmic membrane or to the nucleus (24).

Although it seems that the accumulations in Lafora bodies are responsible for neuronal death in Lafora's disease, it is not clear whether the epilepsy is secondary to neurodegeneration or is a direct result of abnormal neuronal Laforin expression. In various models, both synaptic transmission and key components of neuronal excitability such as the NMDA type of voltage-gated calcium channels appear to be subject to phosphoregulation (19,20).

With 75 of 500 different potential DSPs and PTPs discovered so far, this evolving family of phosphatases is likely to have as diverse and as important a role in various regulatory processes as its counterpart family of protein tyrosine kinases. Biological functions attributed to these proteins so far include regulation of neuronal adhesion, control of axonal pathfinding, regulation of growth factor, cytokine and oligomeric receptor signaling and dephosphorylation of MAP Kinases (MAPKs) and other roles in tumor suppression (16). Involvement of members of this phosphatase family in non-neoplastic diseases has been found in only one other human disorder, namely X-linked myotubular myopathy (21). In this disease, mutations of the DSP MTM1 result in an arrest of muscle maturation in utero after a period of normal development (22).

Laforin is the first member of the family of PTPs and DSPs to bet involved in human central nervous system disease. Further investigation will be necessary to understand its role in normal brain, in the formation of Lafora bodies and in Lafora's disease and its epilepsy.

Example 3
Summary of Common EPM2A Mutations
Patients and methods

Patients reported here had biopsy-proven Lafora's disease. Polymerase chain reaction (PCR) primer sequences and conditions were: JRGXBF: (SEQ ID NO: 9) 5'-TCCATTGTGCTAATGCTATCTC-3', JRGXBR: (SEQ ID NO: 10) 5'-TCAGCTTGCTTTGAGGATATTT-3', H1F: (SEQ ID NO: 7) 5'-GAATGCTCTTTCCACTTTGC-3, PTPR: (SEQ ID NO: 8) 5'-GGCTCCTTAGGGAAATCAG-3'; Annealing: 62°; [MgC12]=1.25 mM. Stock DNA was used; PCR products: were purified on Qiagen columns. Restriction digests were performed at 37°, and products were run on 3% agarose gels.

Results
Mutations

Figure 11:
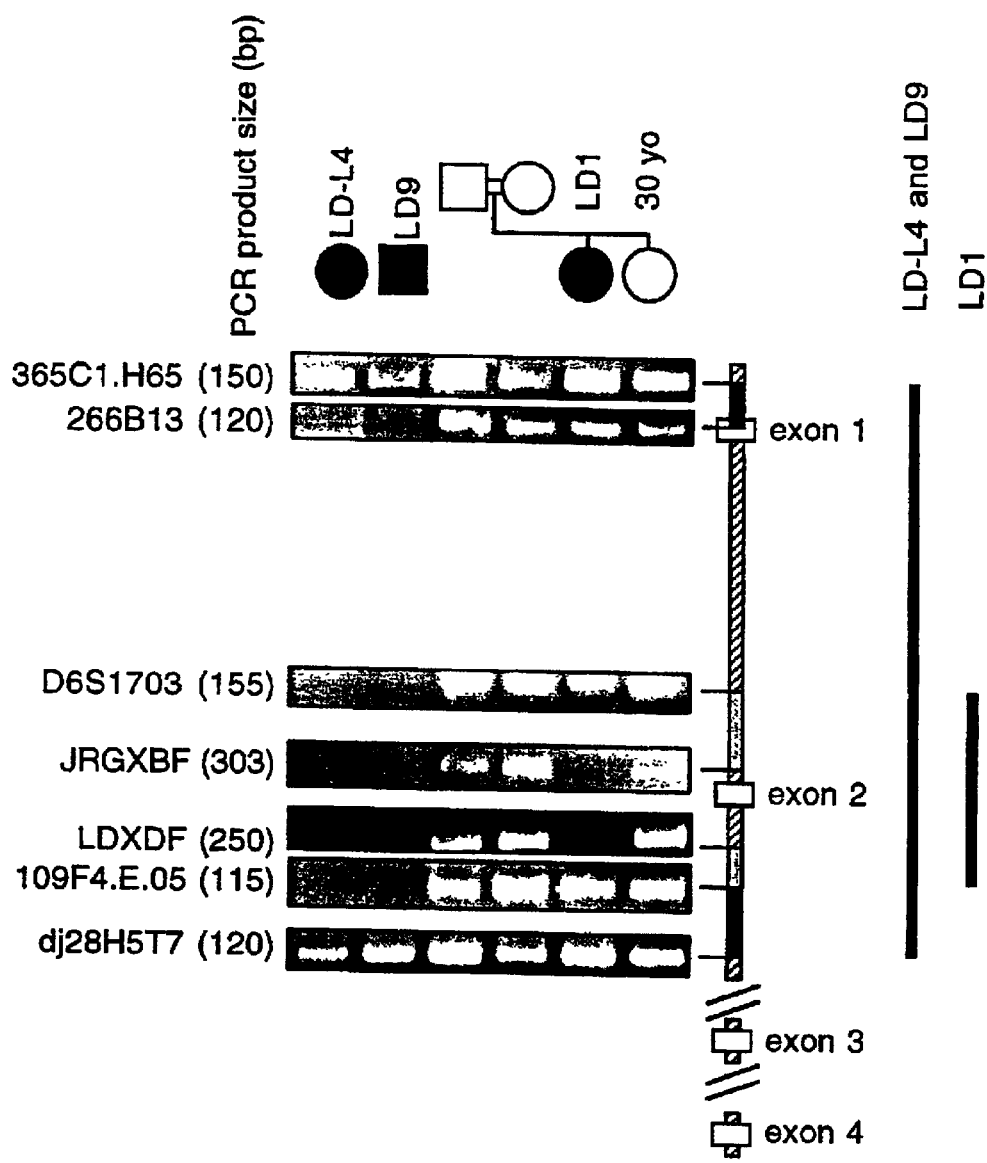
FIG. 11 is a refined map of the deletion breakpoints in families, LD-L4, LD9 and LD1.

EPM2A is composed of 4 exons located within a ~130,000 bp span of ° Chromosome 6q24. FIG. 11 shows a refined map of the deletion breakpoints in families LD-L4, LD9 and LD1. Filled symbols indicate patients with LD. Open rectangles on the map are the exons of EPM2A. Genomic structure around exons 1 and 2 is shown to scale. PCR markers 365C1.H65, 266B13, D6S1703A, JRGBF/R, LDXDF/R, 109F4.E.05 and dj28H5T7 were tested. Primer sequences can be obtained by looking up PAC 466P17 at http://www.sanger.ac.uk. The positions of the forward primers of these markers on the PAC are at: 58336, 59869, 98214, 108805, 123524, 124039 and 132487 bp respectively. The maximum extent of the deletions are shown on the right The deletion breakpoint regions for LD-L4 and LD9 are coloured black on the map and are distinct from the deletion breakpoint regions for LD1 are coloured grey. Each of the four deletion breakpoints contains a MIR repeat As a first step towards screening exon 2 for mutations, it was amplified by PCR with primers JRGXBF and JRGXBR. In the affected members from three families, LD-l4, LD9 and LD1, no PCR product was observed indicating a possible homozygous deletion in these patients. In order to confirm and characterize the extent of this deletion, PCR was performed with primers covering the rest of the gene (FIG. 11). The extent of the deletion in families LD-L4 and LD9 was determined to be ~75,000 bp encompassing both exons 1 and 2. A smaller deletion of ~25,000 bp was found in family LD1.

Screening Tests for the More Common Mutations

FIG. 12 shows restriction endonuclease screening for the two common mutations in exon 4. (A) Restriction map (to scale) of PCR product with primers H1F/PTPR. H, HaeIII restriction enzyme sites one of which is destroyed by the C→T mutation; boxed P, PstI site created by the G→A mutation. (B) HaeIII and PstI digestion of the H1F/PTPR PCR product. Lane 1, 1 Kb ladder, lane 2: normal non-carrier individual with HaeIII digestion, lanes 3 and 4: appearance of an abnormal 199 bp band in a carrier with the C→T mutation (lane 3) and a patient with a homozygous mutation (lane 4); lane 5: PST1 digestion does not affect normal non-carriers, lane 6: PstI digests the PCR product into two smaller fragments in a carrier of the G→A mutation. In patients with a homozygous G→A mutation PSTI digestion should result in the disappearance of the 520 bp original band. However, we presently do not have such a patient in our data set.

The most common EPM2A mutation to date is a C→T nonsense mutation of the second base pair of exon 4 observed in 9 families (Table 2). Primers H1F and PTPR amplify a 520 bp DNA fragment encompassing exon 4 and including several recognition sites for the restriction enzyme HaeIII, one of which is destroyed by the C→T mutation. Digestion of this PCR product with HaeIII in normal non-carrier individuals results in nine small bands the largest of which is 102 bp. Digestion with HaeIII in carriers or patients results in the appearance of an abnormal 199 bp band (FIGS. 12A and 12B). Carriers cannot be distinguished from patients who carry this mutation on both chromosomes using this test (FIG. 12B).

The second most common mutation is a G→A mutation of bp 115 in exon 4 observed in 4 families (Table 2). This mutation creates a unique PstI restriction, site in the sequence of the HIF/PTPR PCR product. PstI does not digest this 520 bp PCR product in normal non-carrier individuals. Carriers will therefore have one normal 520 bp band and two variant bands of 195 bp and 315 bp (FIGS. 12A and 12B). Patients homozygous for this mutation will only have the abnormal bands.

Finally, several families with deletions of EPM2A have been described in Table 2. Two of these families (LD-L4 and LD9) appear to have identical ~75 Kb deletions (FIG. 11), which are different from the other two (Table 2). Nonetheless these three different deletion mutations all encompass exon 2 (FIG. 11, Table 2). Patients homozygous for any of these deletions can be picked up by the absence of PCR amplification using primers JRGXBF/JRGXBR and appropriate controls (FIG. 11).

Discussion

LD is most frequently diagnosed in societies with high rates of consanguinity. There also seems to be an excessive reporting from countries surrounding the Mediterranean basin, and many of those families appear not to be consanguineous. This initially suggested that like other PMEs such as Unverricht-Lundborg disease (27) or the Neuronal Ceroid Lipofuscinoses (28), LD might be caused by a common mutation in most cases. This was shown not to be the case. The large number of different mutations renders their detection for clinical purposes difficult.

The simple DNA-based tests described above can be used to screen for the three more common mutations in the following fashion. Digestion of the HIF/PTPR PCR product with HaeIII and PstI detects the two more common mutations and will confirm that an individual is a carrier of one or the other mutation. The PstI test can further establish whether a patient or fetus is homozygous for the G→A mutation. In order to establish if a patient is homozygous for the mutation detected by the HaeIII test, further analyses will be required such as allele specific oligonucleotide hybridization or DNA sequencing.

PCR using JRGXBF/JRGXBR will detect the deletion mutations described in this report, but only in homozygous state. This simple test can therefore serve for prenatal or symptomatic diagnosis, but cannot detect carriers. For carrier testing in these families further work will be required. For example, in three of the deletions (LD-L4, LD9), the polymorphic microsatellite marker D6S1703 is encompassed in the deletion and can be used to detect carriers by testing for loss of heterozygosity.

The C→T mutation appears to be common in patients of Spanish (or Iberian) origin (Tables 1 and 2). The ~75 Kb deletion was observed in two of two Arabic families in our data set (LD-L4 and LD9). Parenthetically, LD9 is the same Arabic family described in reference 29 in which two affected siblings had discordant biopsy results. While false negative biopsies are usually due to insufficient sampling and/or biopsies done early in the course of the disease, genetic testing should not have these limitations.

Additional EPM2A mutations remain to be found as presently we have identified mutations in only 65% of families. Furthermore, we have recently shown that an altogether different gene other than EPM2A causes LD in up to 20% of patients including the families from the French Canadian province of Quebec (30). These patients are clinically and pathologically indistinguishable from those with EPM2A mutations (30).

Two deletions with different deletion breakpoints are described in this Example. Interestingly, analysis of the sequences of the breakpoint regions revealed the presence of the mammalian-wide interspersed repeat (MIR) (31) in all four breakpoint regions (FIG. 11). Duplicated or repetitive sequences flanking deleted genes or exons of a gene have been implicated in the generation of such deletions due to unequal recombinations. A well-studied example of this from the neurological literature is Hereditary Neuropathy with Liability to Pressure Palsies. The putative mechanism in that deletion is complex involving a large mariner repeat which codes for a transposase that might facilitate the recombination (32). The role, if any, of the short MIR repeats in the generation of the deletions in our LD patients is now under investigation.

In conclusion, the inventors have identified new EPM2A deletion mutations and described DNA-based screening tests for the detection of the more common EPM2A mutations. Further mutations in EPM2A and in the yet unidentified second gene, EPM2B, will improve the role of genetic testing and will provide insights into the function of the gene product laforin and the pathogenesis of LD.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

1. Delgado-Escueta, A. V., Wilson, W. A., Olsen, R. O., Porter, R. J. Jasper's Basic Mechanisms of the Epilepsies (Lippincott-Raven Publishers, 1998) Chapter 1.
2. Berkovic, S. F., Andermann, F., Carpenter, S., and Wolfe, L. S. 1986; Progressive myoclonus epilepsies: specific causes and diagnosis. New Eng. J. Med. 315, 296–305.
3. Minassian, B. A., Sainz, J. and Delgado-Escueta, A. V. 1996. Genetics of Myoclonic and Myoclonus epilepsies. Clin. Neuroscience 3, 223–235.
4. Van Heycop Ten Ham MW. 1974. Lafora disease, a form of progressive myoclonus epilepsy. Handbook of Clinical Neurology 15:382–422.
5. Minassian B A, Sainz J. Bohlega S, Sakamoto L M, Delgado-Escueta A V 1996. Genetic heterogeneity in Lafora's disease. Epilepsia 37 suppl. 5, A126.
6. Lafora, G. R. 1911. Uber das vorkormmen amyloider korperchen im innern der ganglienzellen; zugleich ein beitrag zum studium der amyloiden substanz im nervensystem. Virchows. Arch. Path. Anat., 205, 295–303.
7. Harriman, D. G. and Millar, J. H. D. 1955. Progressive familial myoclonic epilepsy in 3 families: its clinical features and pathological basis. Brain 78, 325–349.
8. Schwarz, G. A. and Yanoff, M. 1965. Lafora's disease, distinct clinico-pathologic form of Unverricht's syndrome. Arch Neurol. 12, 172–188.
9. Carpenter S and Karpati G. 1981. Sweat gland duct cells in Lafora disease: Diagnosis by skin biopsy. Neurol. 31:1564–1568.
10. Sakai, M., Austin, J., Witmer, F. and Trueb, L. 1970. Studies in myoclonus epilepsy (Lafora body form). Neurol. 20, 160–176.
11. Carpenter, S., Karpati, G., Andermann, F., Jacob, J. C. and Andermann, E. 1974 Lafora's disease: peroxisomal storage in skeletal muscle. Neurol. 24, 531–538.
12. Serratosa, J., Delgado-Escueta, A. V., Posada, I., Shih, S., Drury, I., Berciano, J., Zabala, J. A., Antunez, M. C. and Sparkes, R. S. 1995. The gene for progressive myoclonus epilepsy of the Lafora type maps to chromosome 6q. Hum. Molec. Genet 9, 1657–1663.
13. Sainz J., Minassian B. A, Serratosa J. M., Gee M. N., Sakamoto L. M., Iranmanesh R. Bohlega S., Baumann R. J., Ryan S., Sparkes R. S., Delgado-Escueta A. V. 1997. Lafora progressive myoclonus epilepsy: narrowing the chromosome 6q24 locus by recombinations and homozygosities. Am. J. Hum. Genet. 61(5):1205–1209

14. Denu J. M., Stuckey J. A., Saper M. A., Dixon J. E. 1996. Form and Function in Protein dephosphorylation. Cell 87:361–364.

15. Yuvaniyama J., Denu J. M., Dixon J. E., Saper M. A. 1996. Crystal structure of the dual specificity protein phosphatase VHR. Science 272:1328–1331.

16. Tonks N. K., Neel B. G. 1996. From form to function: signaling by protein tyrosine phosphatases. Cell 87:365–368.

17. Yokota T. Ishihara T. Yoshida H. Takahashi M. Uchino F. Hamanaka S. 1988. Monoclonal antibody against polyglucosan isolated from the myocardium of a patient with Lafora disease. J. Neuropath. & Exp. Neurol. 47(5);572–7

18. Thon, V. J., Khalil, M. and Cannon, J. F. 1993. Isolation of human glycogen branching enzyme cDNAs be screening complementation in yeast. J. Biol. Chem. 268, 7509–7513

19. Gurd J. W, Bissoon N. 1997. The N-methyl-D-aspartate receptor subunits NR2A and NR2B bind to the SH2 domains of phospholipase C-gammna. J. of Neurochem. Aug;69(2):623–30

20. Llinas R., Moreno H., Sugimori M., Mohammadi M., Schlessinger J. 1997. Differential pre and postsynaptic modulation of chemical transmission in the squid giant synapse by tyrosine phosphorylation. Proc. Nat. Acad. Sciences (USA) 94(5):1990–1994

21. Laporte J., Hu L. J., Kretz C., Mandel J. L., Kioschis P., Coy J. F., Klauck S. M., Poustka A., Dahl N. 1996. A gene mutated in X-linked myotubular myopathy defines a new putative tyrosine phosphatase family conserved in yeast. Nat. Genet 13(2):175–82

22. Cui X., DeVivo I., Slany R., Miyamoto A., Firestein R., Cleary M L. 1998. Association of SET domain and myotubularin-related proteins modulates growth control. Nat. Genet. 18:331–337

23. M. Kozak, 1996, *Mamm. Genome* 7:563.

24. S. McLaughlin and J. E. Dixon, 1993. *Biol. Chem.*, 268:6839.

25. I. Lopes Cendes et al., 1995, *Epilepsia*, 36:S6.

26. J. N. Acharya, P Satishchandra, S. K. Shankar S K. 1995, *Epilepsia*, 36:429.

27. Lafreniere R G, Rochefort D L, Chretien N et al. Unstable insertion in the 5' flanidng region of the cystatin B gene is the most common mutation in progressive myodonus epilepsy type 1, EPM1. Nat Genet 1997;15:298–302

28. Goebel H H. 7th International Congress on Neuronal Ceroid-Lipofuscinoses (NCL-98), 13–16 Jun. 1998, Dallas, USA Brain Pathol 1998;8:809–810

29. Drury I, Blaivas M, Abou-Khalil B W, Beydoun A. Biopsy results in a kindred with Lafora disease. Arch Neurol 1993;50:102–105

30. Minassian B A, Sainz J, Serratosa J M et al. Genetic locus heterogeneity in Lafora's progessive myoclonus epilepsy. Ann Neurol 1999;45:262–265

31. Smit A F and Riggs A D. MIRs are classic tRNA-derived SINEs that amplifiedbefore the mammalian radiation. Nucleic Acids Res 1995;23:98–102

32. Reiter L T, Murakari T, Koeuth T et al. A recombination hotspot responsible for two inherited peripheral neuropathies is located near a mariner transposon-like element Nature Genet 1996;12:288–297

TABLE 1

Summary of mutations.

| Family | Genetics[1] | Mutation/ (primers used)[2] | Predicted effect |
|---|---|---|---|
| LD-L4 | consanguineous | homozygous deletion (D6S1703 and 109F4.E0.5) | deletion of the majority of EPM2A |
| LD100-4 | consanguineous | homozygous insertion of A resulting in a frameshift (824F and 824R) | interruption of the tyrosine phosphatase domain |
| I-22 | consanguineous | homozygous mutation G → T (JRGXBCF and JRGXBCFR) | glutamic acid → stop |
| LD-33 | consanguineous | homozygous mutation A → T (824F and 824R) | glutamine → leucine |
| LD-5 | consanguineous | homozygous mutation C → T (JRGXBCF and JRGXBCFR) | arginine → cysteine |
| L6 | consanguineous (compound heterozygote) | 1. C → T (824R and H1F) 2. G → A (824F and 824R) | 1. arginine → stop 2. glycine → serine |
| LD-16 | consanguineous | homozygous mutation C → T (824R and H1F) | arginine → stop |
| LD15 | consanguineous | homozygous mutation C → T (824R and H1F) | arginine → stop |
| LD-48 | consanguineous | homozygous mutation C → T (824R and H1F) | arginine → stop |
| LD13 | consanguineous | homozygous mutation C → T (824R and H1F) | arginine → stop |
| L | Italian | heterozygous mutation G to A | **arginine to stop |
| M | | | |
| L B | Non-consanguineous Bolivian ethnicity | **one mutation | **arginine to stop codon (one chromesome) |

[1]Families L6, LD-16, LD15, LD-48 and LD13 are of common ethnic background.
[2]The location of the PCR primers and mutations are shown in FIGS. 3 and 4, respectively.

TABLE 2

Most common EPM2A mutations to date

| | Mutation | n* | Ethnic Origin |
|---|---|---|---|
| 1 | C->T nonsense mutation of bp 2 of exon 4 | 5 2 | Spanish 1 Spanish, 1 Italian |
| 2 | G->A missense mutation of bp115 of exon 4 | 1 | Spanish |
| 3 (a) | ~75 kb deletion | 2 | Arabic |
| (b) | ~25 kb deletion | 1 | Iranian |

Total = 17
*n is the number of families with corresponding mutation

TABLE 3

| Mutation | Nudeotide Position (FIG. 13) | Amino Acid Change (FIG. 14) |
|---|---|---|
| C → T | 721 | Arg (241) → stop |
| insert A | 800 | Premature stop |
| G → A | 836 | Gly (279) → Ser |
| C → T | 163 | Glu → Stop |

TABLE 3-continued

| Mutation | Nucleotide Position (FIG. 13) | Amino Acid Change (FIG. 14) |
|---|---|---|
| T → G | 94 | Trp (32) → Gly |
| A → G | 146 | Asp (49) → Gly |
| G → T | 412 | Glu (138) → stop |
| A → T | 878 | Gln (293) → Leu |
| Delete G | 235 | Premature stop |
| G → A | 179 | Trp (60) → stop |
| C → T | 322 | Arg (108) → Cys |
| C → A | −12 | |
| Deletion (75 kb) | exons 1 and 2 | |
| Deletion (25 kb) | exon 2 | |

We claim:

1. A nucleic acid containing a sequence encoding a protein tyrosine phosphatase which is associated with Lafora's disease having a sequence as shown in SEQ.ID.NO.: 1.

2. An isolated nucleic acid molecule containing a sequence encoding a protein tyrosine phosphatase which is associated with Lafora's disease comprising (a) a nucleic acid sequence as shown in SEQ.ID.NO.: 1, wherein T can also be U;
   (b) nucleic acid sequences complementary to (a); or
   (c) a nucleic acid molecule differing from any of the nucleic acids of (a) or (b) in codon sequences due to the degeneracy of the genetic code.

3. An isolated nucleic acid molecule which is associated with Lafora's disease consisting of a sequence as shown in SEQ ID NO: 3.

4. An isolated nucleic acid molecule which is associated with Lafora's disease consisting of a sequence as shown in SEQ ID NO: 5.

* * * * *

UNITED STATES PATENT AND TRADEMARK OFFICE
CERTIFICATE OF CORRECTION

PATENT NO. : 6,825,328 B1
APPLICATION NO. : 09/744072
DATED : November 30, 2004
INVENTOR(S) : Stephen W. Scherer et al.

It is certified that error appears in the above-identified patent and that said Letters Patent is hereby corrected as shown below:

Title Page, item [76] Inventor: delete "Guy Rouleu" and replace with:
-- Guy Rouleau --

Please insert the following paragraph at Column 1, line 9:

GOVERNMENT SUPPORT
-- This invention was made with Government support of Grant No NS021908 awarded by the National Institutes of Health. The Government has certain rights in this invention. --

Signed and Sealed this

Twenty-fourth Day of March, 2009

JOHN DOLL
*Acting Director of the United States Patent and Trademark Office*

SEQUENCE LISTING

<160> NUMBER OF SEQ ID NOS: 32

<210> SEQ ID NO 1
<211> LENGTH: 3128
<212> TYPE: DNA
<213> ORGANISM: Homo sapiens

<400> SEQUENCE: 1

```
atgcgcttcc gctttggggt ggtggtgcca cccgccgtgg ccggcgcccg gccggagctg      60
ctggtggtgg ggtcgcggcc cgagctgggg cgttgggagc cgcgcggtgc cgtccgcctg     120
aggccggccg gcaccgcggc gggcgacggg gccctggcgc tgcaggagcc gggcctgtgg     180
ctcggggagg tggagctggc ggccgaggag gcggcgcagg acggggcgga gccgggccgc     240
gtggacacgt tctggtacaa gttcctgaag cgggagccgg aggagagct ctcctgggaa      300
ggcaatggac ctcatcatga ccgttgctgt acttacaatg aaaacaactt ggtggatggt     360
gtgtattgtc tcccaatagg acactggatt gaggccactg gcacaccaa tgaaatgaag      420
cacacaacag acttctattt taatattgca ggccaccaag ccatgcatta ttcaagaatt     480
ctaccaaata tctggctggg tagctgccct cgtcaggtgg aacatgttac catcaaactg     540
aagcatgaat tggggattac agctgtaatg aatttccaga ctgaatggga tattgtacag     600
aattcctcag gctgtaaccg ctacccagag cccatgactc agacactat gattaaacta     660
tatagggaag aaggcttggc ctacatctgg atgccaacac cagatatgag caccgaaggc     720
cgagtacaga tgctgcccca ggcggtgtgc ctgctgcatg cgctgctgga aagggacac      780
atcgtgtacg tgcactgcaa cgctggggtg ggccgctcca ccgcggctgt ctgcggctgg     840
ctccagtatg tgatgggctg gaatctgagg aaggtgcagt atttcctcat ggccaagagg     900
ccggctgtct acattgacga agaggccttg gccccgggcac aagaagattt tttccagaaa     960
tttgggaagg ttcgttcttc tgtgtgtagc ctgtagctgg tcagcctgct tctgccccct    1020
cctgatttcc ctaaggagcc tgggatgatg ttggtcaaat gacctagaaa caaggattct    1080
acctgaactg aaaggactgt gtgacctccc caagccaacc actttcacct gggatgactt    1140
tcgattatgc tttggtttgg ggctgtattt ttgaaatact ctacaagaaa gctgtggctc    1200
aacacatgag aagaagcacg aagcagttag gctgtacatc agacagaagg gtaatgcgtg    1260
cagttcctgc tgcctgcagg cagacgaggc ctttgcttta cagcactgta tgtgttgcac    1320
gatggatccg tgacagcact ttcctgttgc actgaaactc ttggccatgt agaggaaaag    1380
```

-continued

```
atatggagtt atgtggattt catcactagt atgtgtgccg tgagctggtc agttgccaaa      1440
ggaggaaata aggttagaag cctgaaccgt acaaaagaa gagctcacta tggtcaaaaa       1500
gtgatggctt tcaggacttg ttttttatcc tgcctcacag ttgttaaagt ctgttccaag      1560
gcatcacctt ccttctctac ccaacaaccc tgtgtaacaa ctaaagtaga attatctctc      1620
atttgttggt ggttttcct caaaattacc aaacaaagca aaaatacccc ttgttttta        1680 tagttgagat gtcaaggaag ttaaattgag gcttaatgag cataggtagc ttgtccaagg     1740
tctcatgacc agtcaagggc aagctggagt taataatcta tatttatttg actcagcact     1800
gttttcatca caacttgttt tcccagcatc atgtagtgca tttagtttg tctttctcag      1860 ggtatagtca atatgcctgc aggagtttct atagcgagac atagaatagt attctgatca     1920
gttgccaaag aatctaggaa attagttgta ttttgtgcaa gctaatttaa aaacatgatg     1980
ggctgtttta agaccagagt ggaaattcat gagaggaact atactaccaa agagcccaa      2040 atgaccaaat ccatggataa ttgcttcaca gccttggcca tcctggctca gctctcaatt    2100
tagtataata tgcagttcct gtgcctccag actatgcagc tcatcaccct aggttctaca    2160
ggaaatacag atgaacaa cttgccttc aaaaatgtg ctgcctagaa acagacctg         2220 catttcaacc caactgtaat gcaggattg gaccatgaat gatatgctag aatagaagaa    2280
agagaagtgt ttttttaatt gagagcctct atgtgcaagg tgatatataa tcatatccag   2340
tttaatcttc acaatatcca atgaagaagg tctcattatc tccatgataa agatggggaa   2400
actaaggtca gaagggttaa ctcaactgtc tattgtcaca tgatgaataa atagatgaag   2460
tgagatacaa agctgggttt gattcaaagc ccttactttc ctaattaaac tatgatgcgt   2520 atttatttt ctgcacccttc cttctttcca caaacacata ttgatagatg caagagactc    2580
ttatttataa ggcgtggggg acaagaagga tacaaggtaa gtttcagtgg agctcagagg   2640
acggggagat agaactgtgg cacttagggg agatgacatt tgctttggc agaggcagct    2700 agccaggaca catttccact ataattttac aaagttaaat ttataagcta gcattaagta   2760
aagtgaagtc cagctccctt gctaaaaata actagaggta ataattggta ttcaggtaac   2820
tcatttacag tcataatgtg ttgtgaaaat ttaatcttaa aaattaaatt tttaaactat   2880
gtgggtctgt gaatttcttt aatgtctaag aaatccagct tcataatttc catgatacaa   2940 agatctttt tcaggtggat ttttacccttt gttcctttg ctctgataga caaaatcagt    3000
ttaggactat taagaatgt tttggaataa actgtctttt tcctcaatga atgggatgtc    3060
taatgtattt caaaatcacc caaaacttt ggcaaataaa agcatttaaa aagaaaaaaa    3120
aaaaaaaa                                                              3128
```

<210> SEQ ID NO 2
<211> LENGTH: 331
<212> TYPE: PRT
<213> ORGANISM: Homo sapiens

<400> SEQUENCE: 2

```
Met Arg Phe Arg Phe Gly Val Val Pro Ala Val Ala Gly Ala
  1               5                  10                  15

Arg Pro Glu Leu Leu Val Val Gly Ser Arg Pro Glu Leu Gly Arg Trp
                 20                  25                  30

Glu Pro Arg Gly Ala Val Arg Leu Arg Pro Ala Gly Thr Ala Ala Gly
             35                  40                  45

Asp Gly Ala Leu Ala Leu Gln Glu Pro Gly Leu Trp Leu Gly Glu Val
         50                  55                  60
```

```
Glu Leu Ala Ala Glu Glu Ala Ala Gln Asp Gly Ala Glu Pro Gly Arg
 65                  70                  75                  80

Val Asp Thr Phe Trp Tyr Lys Phe Leu Lys Arg Glu Pro Gly Gly Glu
             85                  90                  95

Leu Ser Trp Glu Gly Asn Gly Pro His His Asp Arg Cys Cys Thr Tyr
        100                 105                 110

Asn Glu Asn Asn Leu Val Asp Gly Val Tyr Cys Leu Pro Ile Gly His
            115                 120                 125

Trp Ile Glu Ala Thr Gly His Thr Asn Glu Met Lys His Thr Thr Asp
130                 135                 140

Phe Tyr Phe Asn Ile Ala Gly His Gln Ala Met His Tyr Ser Arg Ile
145                 150                 155                 160

Leu Pro Asn Ile Trp Leu Gly Ser Cys Pro Arg Gln Val Glu His Val
                165                 170                 175

Thr Ile Lys Leu Lys His Glu Leu Gly Ile Thr Ala Val Met Asn Phe
            180                 185                 190

Gln Thr Glu Trp Asp Ile Val Gln Asn Ser Ser Gly Cys Asn Arg Tyr
        195                 200                 205

Pro Glu Pro Met Thr Pro Asp Thr Met Ile Lys Leu Tyr Arg Glu Glu
210                 215                 220

Gly Leu Ala Tyr Ile Trp Met Pro Thr Pro Asp Met Ser Thr Glu Gly
225                 230                 235                 240

Arg Val Gln Met Leu Pro Gln Ala Val Cys Leu Leu His Ala Leu Leu
                245                 250                 255

Glu Lys Gly His Ile Val Tyr Val His Cys Asn Ala Gly Val Gly Arg
            260                 265                 270

Ser Thr Ala Ala Val Cys Gly Trp Leu Gln Tyr Val Met Gly Trp Asn
        275                 280                 285

Leu Arg Lys Val Gln Tyr Phe Leu Met Ala Lys Arg Pro Ala Val Tyr
290                 295                 300

Ile Asp Glu Glu Ala Leu Ala Arg Ala Gln Glu Asp Phe Phe Gln Lys
305                 310                 315                 320

Phe Gly Lys Val Arg Ser Ser Val Cys Ser Leu
                325                 330

<210> SEQ ID NO 3
<211> LENGTH: 2940
<212> TYPE: DNA
<213> ORGANISM: Homo sapiens

<400> SEQUENCE: 3
ggtggagctg gcggccgagg aggcggcgca ggacggggcg gagccgggcc gcgtggacac      60
gttctggtac aagttcctga gcgggagcc gggaggagag ctctcctggg aaggcaatgg     120
acctcatcat gaccgttgct gtacttacaa tgaaaacaac ttggtggatg gtgtgtattg     180
tctcccaata ggacactgga ttgaggccac tggacacacc aatgaaatga agcacacaac     240
agacttctat tttaatattg caggccacca agccatgcat tattcaagaa ttctaccaaa     300
tatctggctg ggtagctgcc ctcgacaggt ggaacatgtt accatcaaac tgaagcatga     360 attgggggatt acagctgtca tgaatttcca gactgaatgg gatattgttc agaattcctc     420
atgctgtaac cgctacccag agcccatgac tccagacact atgattaaac tatctaggga     480
agaaggcttg gcctacatct ggatgccaac accagatatg agcaccgcag gccgagtaca     540
gatgctgccc caggcggtgt gcctgctgca tgcgctgctg gagaagggac acatcgtgta     600
```

```
cgtgcactgc aacgctgggg tgggccgctc caccgcggct gtctgcggct ggctccagta    660
tgtgatgggc tggaatctga ggaaggtgca gtatttcctc atggccaaga ggccggctgt    720
ctacattgac gaagaggcct tggcccgggc acaagaagat ttttccaga aatttgggaa     780
ggttcgttct tctgtgtgta gcctgtagct ggtcagcctg cttctgcccc ctcctgattt    840
ccctaaggag cctgggatga tgttggtcaa atgacctaga acaaggatt ctacctgaac     900
tgaaaggact gtgtgacctc cccaagccaa ccactttcac ctgggatgac tttcgattat    960
gctttggttt gggctgtat ttttgaaata ctctacaaga aagctgtggc tcaacacatg    1020
agaagaagca cgaagcagtt aggctgtaca tcagacagaa gggtaatgcg tgcagttcct   1080
gctgcctgca ggcagacgag gcctttgctt tacagcactg tatgtgttgc acgatggatc   1140
cgtgacagca ctttcctgtt gcactgaaac tcttggccat gtagaggaaa agatatggag   1200
ttatgtggat tcatcacta gtatgtgtgc cgtgagctgg tcagttgcca aggaggaaa     1260
taaggttaga agcctgaacc gttacaaaag aagagctcac tatggtcaaa aagtgatggc   1320
tttcaggact tgtttttat cctgcctcac agttgttaaa gtctgttcca aggcatcacc    1380
ttccttctct acccaacaac cctgtgtaac aactaaagta gaattatctc tcatttgttg   1440
gtggttttc ctcaaaatta ccaaacaaag caaaaatac ccttgttttt tatagttgag     1500
atgtcaagga agttaaattg aggcttaatg agcataggta gcttgtccaa ggtctcatga   1560
ccagtcaagg gcaagctgga gttaataatc tatatttatt tgactcagca ctgttttcat   1620
cacaacttgt tttcccagca tcatgtagtg catttagttt tgtctttctc agggtatagt   1680
caatatgcct gcaggagttt ctatagcgag acatagaata gtattctgat cagttgccaa   1740
agaatctagg aaattagttg tattttgtgc aagctaattt aaaaacatga tgggctgttt   1800
taagaccaga gtggaaattc atgagaggaa ctatactacc aaaagagccc aaatgaccaa   1860
atccatggat aattgcttca cagccttggc catcctggct cagctctcaa tttagtataa   1920
tatgcagttc ctgtgcctcc agactatgca gctcatcacc ctaggttcta caggaaatac   1980
agagatgaac aactttgcct tcaaaaaatg tgctgcctag aaaacagacc tgcatttcaa   2040
cccaactgta atgcaggatt tggaccatga atgatatgct agaatagaag aaagagaagt   2100
gtttttttaa ttgagagcct ctatgtgcaa ggtgatatat aatcatatcc agtttaatct   2160
tcacaatatc caatgaagaa ggtctcatta tctccatgat aaagatgggg aaactaaggt   2220
cagaagggtt aactcaactg tctattgtca catgatgaat aaatagatga agtgagatac   2280
aaagctgggt tgattcaaa gcccttactt tcctaattaa actatgatgc gtatttattt    2340
ttctgcacct tcctttcttc cacaaacaca tattgataga tgcaagagac tcttatttat   2400
aaggcgtggg ggacaagaag gatacaaggt aagtttcagt ggagctcaga ggacggggag   2460
atagaactgt ggcacttagg ggagatgaca tttgctttgg gcagaggcag ctagccagga   2520
cacatttcca ctataatttt acaaagttaa atttataagc tagcattaag taaagtgaag   2580
tccagctccc ttgctaaaaa taactagagg taataattgg tattcaggta actcatttac   2640
agtcataatg tgttgtgaaa atttaatctt aaaaattaaa tttttaaact atgtgggtct   2700
gtgaatttct ttaatgtcta agaaatccag cttcataatt tccatgatac aaagatcttt   2760
tttcaggtgg atttttacct tgttcctttt gctctgata gacaaaatca gtttaggact    2820
attaaagaat gttttggaat aaactgtctt tttcctcaat gaatgggatg tctaatgtat   2880
ttcaaaatca cccaaaactt ttggcaaata aaagcattta aaagaaaaa aaaaaaaaa     2940
```

<210> SEQ ID NO 4
<211> LENGTH: 268
<212> TYPE: PRT
<213> ORGANISM: Homo sapiens

<400> SEQUENCE: 4

```
Val Glu Leu Ala Ala Glu Ala Ala Gln Asp Gly Ala Glu Pro Gly
 1               5                  10                  15

Arg Val Asp Thr Phe Trp Tyr Lys Phe Leu Lys Arg Glu Pro Gly Gly
                 20                  25                  30

Glu Leu Ser Trp Glu Gly Asn Gly Pro His His Asp Arg Cys Cys Thr
             35                  40                  45

Tyr Asn Glu Asn Asn Leu Val Asp Gly Val Tyr Cys Leu Pro Ile Gly
         50                  55                  60

His Trp Ile Glu Ala Thr Gly His Thr Asn Glu Met Lys His Thr Thr
 65                  70                  75                  80

Asp Phe Tyr Phe Asn Ile Ala Gly His Gln Ala Met His Tyr Ser Arg
                 85                  90                  95

Ile Leu Pro Asn Ile Trp Leu Gly Ser Cys Pro Arg Gln Val Glu His
                100                 105                 110

Val Thr Ile Lys Leu Lys His Glu Leu Gly Ile Thr Ala Val Met Asn
            115                 120                 125

Phe Gln Thr Glu Trp Asp Ile Val Gln Asn Ser Ser Cys Cys Asn Arg
        130                 135                 140

Tyr Pro Glu Pro Met Thr Pro Asp Thr Met Ile Lys Leu Ser Arg Glu
145                 150                 155                 160

Glu Gly Leu Ala Tyr Ile Trp Met Pro Thr Pro Asp Met Ser Thr Ala
                165                 170                 175

Gly Arg Val Gln Met Leu Pro Gln Ala Val Cys Leu Leu His Ala Leu
            180                 185                 190

Leu Glu Lys Gly His Ile Val Tyr Val His Cys Asn Ala Gly Val Gly
        195                 200                 205

Arg Ser Thr Ala Ala Val Cys Gly Trp Leu Gln Tyr Val Met Gly Trp
210                 215                 220

Asn Leu Arg Lys Val Gln Tyr Phe Leu Met Ala Lys Arg Pro Ala Val
225                 230                 235                 240

Tyr Ile Asp Glu Glu Ala Leu Ala Arg Ala Gln Glu Asp Phe Phe Gln
                245                 250                 255

Lys Phe Gly Lys Val Arg Ser Ser Val Cys Ser Leu
            260                 265
```

<210> SEQ ID NO 5
<211> LENGTH: 915
<212> TYPE: DNA
<213> ORGANISM: Homo sapiens

<400> SEQUENCE: 5

```
ccaagaatcg gcacgaggat tattcaagaa ttctaccaaa tatctggctg ggtagctgcc      60
ctcgacaggt ggaacatgtt accatcaaac tgaagcatga attggggatt acagctgtca     120
tgaatttcca gactgaatgg gatattgttc agaattcctc atgctgtaac cgctacccag     180
agcccatgac tccagacact atgattaaac tatctaggga agaaggcttg gcctacatct     240
ggatgccaac accagatatg agcaccgcag gccgagtaca gatgctgccc caggcggtgt     300
gcctgctgca tgcgctgctg gagaagggac acatcgtgta cgtgcactgc aacgctgggg     360
```

```
tgggccgctc caccgcggct gtctgcggct ggctccagta tgtgatgggc tggaatctga      420
ggaaggtgca gtatttcctc atggccaaga ggccggctgt ctacattgac gaagaggcag      480
ctagccagga cacatttcca ctataatttt acaaagttaa atttataagc tagcattaag      540
taaagtgaag tccagctccc ttgctaaaaa taactagagg taataattgg tattcaggta      600
actcatttac agtcataatg tgttgtgaaa atttaatctt aaaaattaaa tttttaaact      660
atgtgggtct gtgaatttct ttaatgtcta agaaatccag cttcataatt tccatgatac      720
aaagatcttt tttcaggtgg attttttacct ttgttccttt tgctctgata gacaaaatca     780
gtttaggact attaaagaat gttttggaat aaactgtctt tttcctcaat gaatgggatg      840
tctaatgtat ttcaaaatca cccaaaactt ttggcaaata aagcattta aaaagaaaaa       900 aaaaaaaaaa aaaaa                                                       915
```

<210> SEQ ID NO 6
<211> LENGTH: 167
<212> TYPE: PRT
<213> ORGANISM: Homo sapiens

<400> SEQUENCE: 6

```
Lys Asn Arg His Glu Asp Tyr Ser Arg Ile Leu Pro Asn Ile Trp Leu
  1               5                  10                  15

Gly Ser Cys Pro Arg Gln Val Glu His Val Thr Ile Lys Leu Lys His
             20                  25                  30

Glu Leu Gly Ile Thr Ala Val Met Asn Phe Gln Thr Glu Trp Asp Ile
         35                  40                  45

Val Gln Asn Ser Ser Cys Cys Asn Arg Tyr Pro Glu Pro Met Thr Pro
     50                  55                  60

Asp Thr Met Ile Lys Leu Ser Arg Glu Glu Gly Leu Ala Tyr Ile Trp
 65                  70                  75                  80

Met Pro Thr Pro Asp Met Ser Thr Ala Gly Arg Val Gln Met Leu Pro
                 85                  90                  95

Gln Ala Val Cys Leu Leu His Ala Leu Leu Glu Lys Gly His Ile Val
            100                 105                 110

Tyr Val His Cys Asn Ala Gly Val Gly Arg Ser Thr Ala Ala Val Cys
        115                 120                 125

Gly Trp Leu Gln Tyr Val Met Gly Trp Asn Leu Arg Lys Val Gln Tyr
    130                 135                 140

Phe Leu Met Ala Lys Arg Pro Ala Val Tyr Ile Asp Glu Glu Ala Ala
145                 150                 155                 160

Ser Gln Asp Thr Phe Pro Leu
                165
```

<210> SEQ ID NO 7
<211> LENGTH: 20
<212> TYPE: DNA
<213> ORGANISM: Homo sapiens

<400> SEQUENCE: 7

```
gaatgctctt tccactttgc                                                   20
```

<210> SEQ ID NO 8
<211> LENGTH: 19
<212> TYPE: DNA
<213> ORGANISM: Homo sapiens

<400> SEQUENCE: 8

```
ggctccttag ggaaatcag                                            19

<210> SEQ ID NO 9
<211> LENGTH: 22
<212> TYPE: DNA
<213> ORGANISM: Homo sapiens

<400> SEQUENCE: 9
tccattgtgc taatgctatc tc                                        22

<210> SEQ ID NO 10
<211> LENGTH: 22
<212> TYPE: DNA
<213> ORGANISM: Homo sapiens

<400> SEQUENCE: 10
tcagcttgct ttgaggatat tt                                        22

<210> SEQ ID NO 11
<211> LENGTH: 20
<212> TYPE: DNA
<213> ORGANISM: Homo sapiens

<400> SEQUENCE: 11
cggcacgagg attattcaag                                           20

<210> SEQ ID NO 12
<211> LENGTH: 19
<212> TYPE: DNA
<213> ORGANISM: Homo sapiens

<400> SEQUENCE: 12
gctcgggtac tgaggtctg                                            19

<210> SEQ ID NO 13
<211> LENGTH: 22
<212> TYPE: DNA
<213> ORGANISM: Homo sapiens

<400> SEQUENCE: 13
agttgttaca cagggttgtt gg                                        22

<210> SEQ ID NO 14
<211> LENGTH: 22
<212> TYPE: DNA
<213> ORGANISM: Homo sapiens

<400> SEQUENCE: 14
aggctgtaca tcagacagaa gg                                        22

<210> SEQ ID NO 15
<211> LENGTH: 22
<212> TYPE: DNA
<213> ORGANISM: Homo sapiens

<400> SEQUENCE: 15
tccattgtgc taatgctatc tc                                        22

<210> SEQ ID NO 16
<211> LENGTH: 22
<212> TYPE: DNA
<213> ORGANISM: Homo sapiens

<400> SEQUENCE: 16
```

-continued

```
tcagcttgct ttgaggatat tt                                              22

<210> SEQ ID NO 17
<211> LENGTH: 19
<212> TYPE: DNA
<213> ORGANISM: Homo sapiens

<400> SEQUENCE: 17
gccgagtaca gatgctgcc                                                  19

<210> SEQ ID NO 18
<211> LENGTH: 22
<212> TYPE: DNA
<213> ORGANISM: Homo sapiens

<400> SEQUENCE: 18
cacacagtcc tttcagttca gg                                              22

<210> SEQ ID NO 19
<211> LENGTH: 33
<212> TYPE: DNA
<213> ORGANISM: Homo sapiens

<400> SEQUENCE: 19
gcccgggtat tcgcgccgcc gccgcccgcc atg                                  33

<210> SEQ ID NO 20
<211> LENGTH: 19
<212> TYPE: DNA
<213> ORGANISM: Homo sapiens

<400> SEQUENCE: 20
atcatgaccg ttgctgtac                                                  19

<210> SEQ ID NO 21
<211> LENGTH: 21
<212> TYPE: DNA
<213> ORGANISM: Homo sapiens

<400> SEQUENCE: 21
tcatcatgac tgttgctgta c                                               21

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (3)..(4)
<223> OTHER INFORMATION: Any amino acid
<221> NAME/KEY: MOD_RES
<222> LOCATION: (6)..(7)
<223> OTHER INFORMATION: Any amino acid

<400> SEQUENCE: 22

His Cys Xaa Xaa Gly Xaa Xaa Arg Ser Thr
 1               5                  10

<210> SEQ ID NO 23
<211> LENGTH: 10
<212> TYPE: RNA
<213> ORGANISM: Artificial Sequence
<220> FEATURE:
```

```
<223> OTHER INFORMATION: Description of Artificial Sequence: Consensus
      sequence

<400> SEQUENCE: 23
cccgccaugc                                                            10

<210> SEQ ID NO 24
<211> LENGTH: 10
<212> TYPE: RNA
<213> ORGANISM: Artificial Sequence
<220> FEATURE:
<223> OTHER INFORMATION: Description of Artificial Sequence: Consensus
      sequence

<400> SEQUENCE: 24 gccrccaugg                                                            10

<210> SEQ ID NO 25
<211> LENGTH: 22
<212> TYPE: PRT
<213> ORGANISM: Homo sapiens

<400> SEQUENCE: 25

Leu Ala Arg Ala Gln Glu Asp Phe Phe Gln Lys Phe Gly Lys Val Arg
 1               5                  10                  15
Ser Ser Val Cys Ser Leu
            20

<210> SEQ ID NO 26
<211> LENGTH: 8
<212> TYPE: PRT
<213> ORGANISM: Homo sapiens

<400> SEQUENCE: 26

Ala Ser Gln Asp Thr Phe Pro Leu
 1               5

<210> SEQ ID NO 27
<211> LENGTH: 11
<212> TYPE: PRT
<213> ORGANISM: Homo sapiens

<400> SEQUENCE: 27

Val His Cys Asn Ala Gly Val Gly Arg Ser Thr
 1               5                  10

<210> SEQ ID NO 28
<211> LENGTH: 11
<212> TYPE: PRT
<213> ORGANISM: Homo sapiens

<400> SEQUENCE: 28

Val His Cys Ser Asp Gly Trp Asp Arg Thr Ala
 1               5                  10

<210> SEQ ID NO 29
<211> LENGTH: 11
<212> TYPE: PRT
<213> ORGANISM: Homo sapiens

<400> SEQUENCE: 29

Ile His Cys Lys Ala Gly Lys Gly Arg Thr Gly
 1               5                  10

<210> SEQ ID NO 30
```

-continued

```
<211> LENGTH: 11
<212> TYPE: PRT
<213> ORGANISM: Homo sapiens

<400> SEQUENCE: 30

Val His Cys Ser Ala Gly Ile Gly Arg Ser Gly
 1               5                  10

<210> SEQ ID NO 31
<211> LENGTH: 11
<212> TYPE: PRT
<213> ORGANISM: Homo sapiens

<400> SEQUENCE: 31

Val His Cys Ser Ala Gly Ile Gly Arg Ser Gly
 1               5                  10

<210> SEQ ID NO 32
<211> LENGTH: 11
<212> TYPE: PRT
<213> ORGANISM: Homo sapiens

<400> SEQUENCE: 32

Val His Cys Gln Ala Gly Ile Ser Arg Ser Ala
 1               5                  10
```